(12) United States Patent
Beyrard

(10) Patent No.: US 7,796,794 B2
(45) Date of Patent: Sep. 14, 2010

(54) METHOD FOR REDUCING EXPOSURE TO INFRARED LIGHT BEAM, ULTRASOUND OR MAGNETIC IMPULSE RAYS IN MEDICAL IMAGING DEVICES

(76) Inventor: Norbert Beyrard, 170, avenue des Thermes, Divonne-les-Bains (FR) F-01220

( * ) Notice: Subject to any disclaimer, the term of this patent is extended or adjusted under 35 U.S.C. 154(b) by 943 days.

(21) Appl. No.: 11/610,717

(22) Filed: Dec. 14, 2006

(65) Prior Publication Data

US 2007/0116340 A1    May 24, 2007

Related U.S. Application Data

(63) Continuation of application No. PCT/FR2005/001437, filed on Jun. 10, 2005.

(30) Foreign Application Priority Data

Jun. 16, 2004  (FR)  ................... 04 06497
Nov. 18, 2004  (FR)  ................... 04 52677

(51) Int. Cl.
*G06K 9/00* (2006.01)
(52) U.S. Cl. ...................... 382/128; 378/62
(58) Field of Classification Search ............... 600/300, 600/407; 128/920; 378/1, 37, 21, 41, 42, 378/38, 44, 51, 62, 65, 146; 382/100, 128, 382/129, 130, 131, 132, 133, 134, 173, 181
See application file for complete search history.

(56) References Cited

U.S. PATENT DOCUMENTS 5,241,471 A    8/1993   Trousset (Continued)

FOREIGN PATENT DOCUMENTS

EP    0964366    12/1999

(Continued)

OTHER PUBLICATIONS

Jiang M et al: "Convergence Studies on Iterative Algorithms for Image Reconstruction"—IEEE Transactions on Medical Imaging, IEEE Inc. NY, US., pp. 569-579.

(Continued)

*Primary Examiner*—Andrew W Johns
*Assistant Examiner*—Tahmina Ansari
(74) *Attorney, Agent, or Firm*—Sturm & Fix LLP

(57) ABSTRACT

Method and apparatus for X-ray imaging of a body, employing a support to receive a body to be examined, a source emitting a beam of X-rays, a detector irradiated by the beam, a converter for converting the detected intensities into data, a means for turning the mounted mobile support by an angle of rotation about an axis of rotation with respect to the source and the detector and a suitably programmed computer to average the data acquired for a pair of orthogonal angles of rotation to obtain n column and m line mean values for n and m elementary segments of a band of the detector, to construct an initial image (n, m) with the n column and m line mean values, to adjust the coefficient of attenuation in each n×m elementary zone by a method of least squares taking into account the n column and m line mean values regarded as constraints, to repeat the previous stages for data acquired with different pairs of preferably orthogonal angles of rotation, and to average term by term the adjusted images so as to arrive at a synthesis image expressing coefficients of attenuation of the examined body.

13 Claims, 19 Drawing Sheets

U.S. PATENT DOCUMENTS

| | | | |
|---|---|---|---|
| 5,442,674 A | | 8/1995 | Picard |
| 5,737,456 A | * | 4/1998 | Carrington et al. ........... 382/299 |
| 6,970,597 B1 | * | 11/2005 | Olding et al. ............... 382/167 |
| 7,352,919 B2 | * | 4/2008 | Zhou et al. .................. 382/299 |
| 2003/0002707 A1 | * | 1/2003 | Reed et al. .................. 382/100 |
| 2005/0013509 A1 | * | 1/2005 | Samadani ................... 382/302 |
| 2005/0261571 A1 | * | 11/2005 | Willis et al. ................. 600/411 |
| 2006/0253013 A1 | * | 11/2006 | Cable et al. ................. 600/407 |

FOREIGN PATENT DOCUMENTS

| | | |
|---|---|---|
| EP | 1096428 | 5/2001 |

OTHER PUBLICATIONS

Gordon R: "A Tutorial on Art"—IEEE Transactions on Nuclear Science, IEEE Inc. NY, US. pp. 78-93.

Herman G T et al: "Albebraic Reconstruction Techniques Can Be Made Computationally Efficient"—IEEE Transactions on Medical Imaging, IEEE Inc., NY, US. pp. 600-609.

* cited by examiner

Fig. 17

|    | 1    | 2    | 3    | 4    | 5    | 6    | 7    | 8    | 9    | 10   | 11   | 12   | 13   | 14   | 15   | 16   | 17   | 18   | 19  | 20  | 21   |
|----|------|------|------|------|------|------|------|------|------|------|------|------|------|------|------|------|------|------|-----|-----|------|
| 1  | 0,88 | 0,88 | 0,88 | 0,88 | 0,88 | 0,96 | 0,96 | 0,96 | 0,96 | 0,96 | 0,72 | 0,72 | 0,72 | 0,72 | 0,72 | 0,64 | 0,64 | 0,64 | 0,6 | 0,6 | 16   |
| 2  | 0,88 | 0,88 | 0,88 | 0,88 | 0,88 | 0,96 | 0,96 | 0,96 | 0,96 | 0,96 | 0,72 | 0,72 | 0,72 | 0,72 | 0,72 | 0,64 | 0,64 | 0,64 | 0,6 | 0,6 | 16   |
| 3  | 0,88 | 0,88 | 0,88 | 0,88 | 0,88 | 0,96 | 0,96 | 0,96 | 0,96 | 0,96 | 0,72 | 0,72 | 0,72 | 0,72 | 0,72 | 0,64 | 0,64 | 0,64 | 0,6 | 0,6 | 16   |
| 4  | 0,88 | 0,88 | 0,88 | 0,88 | 0,88 | 0,96 | 0,96 | 0,96 | 0,96 | 0,96 | 0,72 | 0,72 | 0,72 | 0,72 | 0,72 | 0,64 | 0,64 | 0,64 | 0,6 | 0,6 | 16   |
| 5  | 0,88 | 0,88 | 0,88 | 0,88 | 0,88 | 0,96 | 0,96 | 0,96 | 0,96 | 0,96 | 0,72 | 0,72 | 0,72 | 0,72 | 0,72 | 0,64 | 0,64 | 0,64 | 0,6 | 0,6 | 16   |
| 6  | 0,96 | 0,96 | 0,96 | 0,96 | 0,96 | 0,88 | 0,88 | 0,88 | 0,88 | 0,88 | 0,72 | 0,72 | 0,72 | 0,72 | 0,72 | 0,8  | 0,8  | 0,8  | 0,8 | 0,8 | 16,8 |
| 7  | 0,96 | 0,96 | 0,96 | 0,96 | 0,96 | 0,88 | 0,88 | 0,88 | 0,88 | 0,88 | 0,72 | 0,72 | 0,72 | 0,72 | 0,72 | 0,8  | 0,8  | 0,8  | 0,8 | 0,8 | 16,8 |
| 8  | 0,96 | 0,96 | 0,96 | 0,96 | 0,96 | 0,88 | 0,88 | 0,88 | 0,88 | 0,88 | 0,72 | 0,72 | 0,72 | 0,72 | 0,72 | 0,8  | 0,8  | 0,8  | 0,8 | 0,8 | 16,8 |
| 9  | 0,96 | 0,96 | 0,96 | 0,96 | 0,96 | 0,88 | 0,88 | 0,88 | 0,88 | 0,88 | 0,72 | 0,72 | 0,72 | 0,72 | 0,72 | 0,8  | 0,8  | 0,8  | 0,8 | 0,8 | 16,8 |
| 10 | 0,96 | 0,96 | 0,96 | 0,96 | 0,96 | 0,88 | 0,88 | 0,88 | 0,88 | 0,88 | 0,72 | 0,72 | 0,72 | 0,72 | 0,72 | 0,8  | 0,8  | 0,8  | 0,8 | 0,8 | 16,8 |
| 11 | 1,04 | 1,04 | 1,04 | 1,04 | 1,04 | 0,8  | 0,8  | 0,8  | 0,8  | 0,8  | 0,88 | 0,88 | 0,88 | 0,88 | 0,88 | 0,96 | 0,96 | 0,96 | 1   | 1   | 18,4 |
| 12 | 1,04 | 1,04 | 1,04 | 1,04 | 1,04 | 0,8  | 0,8  | 0,8  | 0,8  | 0,8  | 0,88 | 0,88 | 0,88 | 0,88 | 0,88 | 0,96 | 0,96 | 0,96 | 1   | 1   | 18,4 |
| 13 | 1,04 | 1,04 | 1,04 | 1,04 | 1,04 | 0,8  | 0,8  | 0,8  | 0,8  | 0,8  | 0,88 | 0,88 | 0,88 | 0,88 | 0,88 | 0,96 | 0,96 | 0,96 | 1   | 1   | 18,4 |
| 14 | 1,04 | 1,04 | 1,04 | 1,04 | 1,04 | 0,8  | 0,8  | 0,8  | 0,8  | 0,8  | 0,88 | 0,88 | 0,88 | 0,88 | 0,88 | 0,96 | 0,96 | 0,96 | 1   | 1   | 18,4 |
| 15 | 1,04 | 1,04 | 1,04 | 1,04 | 1,04 | 0,8  | 0,8  | 0,8  | 0,8  | 0,8  | 0,88 | 0,88 | 0,88 | 0,88 | 0,88 | 0,96 | 0,96 | 0,96 | 1   | 1   | 18,4 |
| 16 | 14,4 | 14,4 | 14,4 | 14,4 | 14,4 | 13,2 | 13,2 | 13,2 | 13,2 | 13,2 | 11,6 | 11,6 | 11,6 | 11,6 | 11,6 | 12   | 12   | 12   | 12  | 12  | 256  |
| 17 |      |      |      |      |      |      |      |      |      |      |      |      |      |      |      |      |      |      |     |     |      |
| 18 |      |      |      |      |      |      |      |      |      |      |      |      |      |      |      |      |      |      |     |     |      |

Fig. 18

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 1 | 0,88 | 0,88 | 0,88 | 0,88 | 0,88 | 1 | 0,96 | 0,96 | 0,96 | 0,96 | 0,7 | 0,7 | 0,72 | 0,7 | 0,7 | 0,64 | 0,64 | 0,64 | 0,64 | 0,64 | 16 | 18,8 |
| 2 | 0,88 | 0,88 | 0,88 | 0,88 | 0,88 | 1 | 0,96 | 0,96 | 0,96 | 0,96 | 0,7 | 0,7 | 0,72 | 0,7 | 0,7 | 0,64 | 0,64 | 0,64 | 0,64 | 0,64 | 16 | 18 |
| 3 | 0,88 | 0,88 | 0,88 | 0,88 | 0,88 | 1 | 0,96 | 0,96 | 0,96 | 0,96 | 0,7 | 0,7 | 0,72 | 0,7 | 0,7 | 0,64 | 0,64 | 0,64 | 0,64 | 0,64 | 16 | 14 |
| 4 | 0,88 | 0,88 | 0,88 | 0,88 | 0,88 | 1 | 0,96 | 0,96 | 0,96 | 0,96 | 0,7 | 0,7 | 0,72 | 0,7 | 0,7 | 0,64 | 0,64 | 0,64 | 0,64 | 0,64 | 16 | 14 |
| 5 | 0,88 | 0,88 | 0,88 | 0,88 | 0,88 | 1 | 0,96 | 0,96 | 0,96 | 0,96 | 0,7 | 0,7 | 0,72 | 0,7 | 0,7 | 0,64 | 0,64 | 0,64 | 0,64 | 0,64 | 16 | 18 |
| 6 | 0,88 | 0,88 | 0,88 | 0,88 | 0,88 | 1 | 0,88 | 0,96 | 0,96 | 0,96 | 0,7 | 0,7 | 0,72 | 0,7 | 0,7 | 0,64 | 0,64 | 0,64 | 0,64 | 0,64 | 16 | 16 |
| 7 | 0,96 | 0,96 | 0,96 | 0,96 | 0,96 | 0,9 | 0,88 | 0,88 | 0,88 | 0,88 | 0,7 | 0,7 | 0,72 | 0,7 | 0,7 | 0,8 | 0,8 | 0,8 | 0,8 | 0,8 | 16,8 | 18,8 |
| 8 | 0,96 | 0,96 | 0,96 | 0,96 | 0,96 | 0,9 | 0,88 | 0,88 | 0,88 | 0,88 | 0,7 | 0,7 | 0,72 | 0,7 | 0,7 | 0,8 | 0,8 | 0,8 | 0,8 | 0,8 | 16,8 | 14,8 |
| 9 | 0,96 | 0,96 | 0,96 | 0,96 | 0,96 | 0,9 | 0,88 | 0,88 | 0,88 | 0,88 | 0,7 | 0,7 | 0,72 | 0,7 | 0,7 | 0,8 | 0,8 | 0,8 | 0,8 | 0,8 | 16,8 | 14,8 |
| 10 | 0,96 | 0,96 | 0,96 | 0,96 | 0,96 | 0,9 | 0,88 | 0,88 | 0,88 | 0,88 | 0,7 | 0,7 | 0,72 | 0,7 | 0,7 | 0,8 | 0,8 | 0,8 | 0,8 | 0,8 | 16,8 | 18,8 |
| 11 | 1,04 | 1,04 | 1,04 | 1,04 | 1,04 | 0,8 | 0,8 | 0,8 | 0,8 | 0,8 | 0,9 | 0,9 | 0,88 | 0,9 | 0,9 | 0,96 | 0,96 | 0,96 | 0,96 | 0,96 | 16,8 | 16,8 |
| 12 | 1,04 | 1,04 | 1,04 | 1,04 | 1,04 | 0,8 | 0,8 | 0,8 | 0,8 | 0,8 | 0,9 | 0,9 | 0,88 | 0,9 | 0,9 | 0,96 | 0,96 | 0,96 | 0,96 | 0,96 | 18,4 | 20,4 |
| 13 | 1,04 | 1,04 | 1,04 | 1,04 | 1,04 | 0,8 | 0,8 | 0,8 | 0,8 | 0,8 | 0,9 | 0,9 | 0,88 | 0,9 | 0,9 | 0,96 | 0,96 | 0,96 | 0,96 | 0,96 | 18,4 | 16,4 |
| 14 | 1,04 | 1,04 | 1,04 | 1,04 | 1,04 | 0,8 | 0,8 | 0,8 | 0,8 | 0,8 | 0,9 | 0,9 | 0,88 | 0,9 | 0,9 | 0,96 | 0,96 | 0,96 | 0,96 | 0,96 | 18,4 | 16,4 |
| 15 | 1,04 | 1,04 | 1,04 | 1,04 | 1,04 | 0,8 | 0,8 | 0,8 | 0,8 | 0,8 | 0,9 | 0,9 | 0,88 | 0,9 | 0,9 | 0,96 | 0,96 | 0,96 | 0,96 | 0,96 | 18,4 | 20,4 |
| 16 | 14,4 | 14,4 | 14,4 | 14,4 | 14,4 | 13 | 13,2 | 13,2 | 13,2 | 13,2 | 12 | 12 | 11,6 | 11 | 12 | 12 | 12 | 12 | 12 | 12 | 18,4 | 18,4 |
| 17 | 13,6 | 14,4 | 13,8 | 13,6 | 15,2 | 13 | 14 | 13,6 | 12,8 | 12,6 | 12 | 13 | 12,4 | 11 | 11 | 11,4 | 12 | 12,4 | 12,8 | 11,6 | 256 | 256 |
| 18 | 13,6 | 28 | 41,8 | 55,4 | 70,6 | 84 | 97,6 | 111 | 124 | 137 | 148 | 161 | 173 | 184 | 196 | 207 | 219 | 231,4 | 244,2 | 255,8 | | |
| 19 | 14,4 | 28,8 | 43,2 | 57,6 | 72 | 85 | 98,4 | 112 | 125 | 138 | 150 | 161 | 173 | 184 | 196 | 208 | 220 | 232 | 244 | 256 | | |

METHOD FOR REDUCING EXPOSURE TO INFRARED LIGHT BEAM, ULTRASOUND OR MAGNETIC IMPULSE RAYS IN MEDICAL IMAGING DEVICES

CROSS REFERENCE TO RELATED APPLICATIONS

This application is a Continuation application of PCT/FR2005/001437 filed Jun. 10, 2005, which claims priority of Application Nos. FR0406497 filed Jun. 16, 2004; FR0452677 filed Nov. 18, 2004, which are all incorporated by reference herein in their entirety.

BACKGROUND OF THE INVENTION

1. Field of the Invention

The present invention relates to a method intended to reduce the exposure of an organism to radiation and infra-red, ultrasonic or magnetic pulse beams from medical imaging equipment, and comprises a method for treating a signal or a set of signals with a view to producing under greatly improved conditions digital images of the interior of an organism, in order to detect and treat where appropriate abnormalities or disorders in the examined organism.

2. Description of the Related Art

Various methods are now commonly used for this purpose, in particular radiography, scanography, echography and magnetic resonance imaging, in order to obtain and process information relating to a set of points or elementary zones located in an organism, so as to produce items of information relating to each point and capable of being reproduced in the form of images that can be used by medical practitioners to investigate abnormalities or disorders.

Conventionally a value, associated with each point or zone, of the coefficient of attenuation in the case of a medical scanner, of reflection in the case of echography, or of the proton density in the case of magnetic resonance imaging, is obtained by means of a suitable calculation in order to produce an internal image of the organism.

The example of the medical scanner illustrates the prior art in this respect.

Medical imaging is in fact a basic procedure for detecting and treating cancer and a certain number of serious conditions, or observing the internal organs of a patient. However, the medical community have felt it necessary to go much further in expressing the need for a high definition medical imaging method in order to achieve a significant improvement in obtaining and processing signals and images that they represent.

The principles of scanography and the current state of the art in this field should first of all be recalled.

Scanography (or tomodensitometry) was discovered in 1968 by G. N. Hounsfield, an engineer working for the EMI company.

The 1972 patent (U.S. Pat. No. 3,924,131, U.S. Pat. No. 3,919,552) is entitled "A method and apparatus for examination of a body by radiation such as X or gamma-radiation".

In 1979 the inventor was awarded the Nobel prize for his invention.

The principle of the invention is as follows:

A beam of X-rays scans a defined plane, passes linearly through an organ, and strikes a plate or a radiographic detector. The passage through the organ produces an attenuation of the beam, the degree of attenuation being able to be measured by means of the detector. Crosswise scanning in the sectional plane produces a set of information that is processed by suitable software on an associated computer.

In fact, in a heterogeneous medium the attenuation along each scanning axis may be expressed by an exponential law, taking into account the photoelectric absorption and diffusion due to the Compton effect.

Let I0 be the reference value, Ix be the value at a point X, then one may write the following relationship:

$$\int A(x)dx = F \; I = Ioe^{-F} \; In = IoE$$

From which one obtains by discretisation:

$$Ln\frac{Io}{In} = \int_0^r A(x)dx = A_1 X_1 + A_2 X_2 + \ldots + A_n X_n$$

The successive values $A_1, A_2, \ldots, A_n$ correspond to the values of each segment defined by $X_1, X_2, \ldots, X_n$.

The profiles of each scanning associated with a specific angle (or a specific position) may then be expressed by a series of equations.

A particular scale may be defined by the value relative to a reference value of the coefficient of attenuation, for example that of water or any other suitably chosen molecule.

The scale most often used is that relating to an abundant molecule in all living organisms, namely water.

If $A(H_2O)$ denotes the coefficient of attenuation of water, then a relative scale such as the following may be used:

$$Bn = [An - A(H_2O)] * 1000 / A(H_2O)$$

The value of the coefficient of water may be defined as equal to 1 or 0, thereby creating a notation system that is easy to use since water is an essential component of the human body.

Other systems may however be used, according to the way in which the information obtained is expressed (visually). Often a value of 1000 is chosen for bone and a value of −1000 is chosen for air.

The information processing of a sufficient number of cross scannings, defining in fact small elementary cells or zones, enables a set of linear equations to be solved provided that the number of scannings is equal to the number of cells.

The editing and use of the information are carried out by an associated computer.

The computer collects the set of data and then calculates the value of the coefficient of attenuation of each elementary zone.

The information obtained from these calculations is expressed by a map of the tomographic sectional plane.

The set of maps constitutes the three-dimensional scanner image of the analysis, which permits longitudinal or transverse sections.

The medical interpretation is thus based on a real internal image of the tissues.

Such images enable the condition of certain bones, as well as the condition of the brain, to be checked in order to detect a tumour or other anomaly.

The investigations are preceded or completed by other investigations, for example ultrasound echography or magnetic resonance imaging.

Scanning and the methods that it has introduced remain an essential tool of medical investigation.

At the start, a series of angular displacements of the order of 3° were carried out, repeated some hundred times.

The improvements that have been introduced since then enable a plurality of beams to be combined with detection strips of a sufficient length so as to multiply the number of measurements made at any one time thanks to multiple detectors.

In the fifth generation scanners detector strips are used perpendicular to the sectional plane in order to prevent any shift or displacement.

The image that is obtained is the result of a stepwise process:
obtaining values of the attenuations for each projection;
calculations of the values of a profile;
matrix representation of each sectional plane;
conversion of each representation by means of a specific map;
establishment of a spatial cartographic system.

Nowadays volumes of each elementary zone of the order of $mm^3$ are obtained. However, this is far from the microscopic scale since the number of living cells is of the order of 1 billion per $mm^3$.

An example of such a scanner is described in the document U.S. Pat. No. 5,241,471. According to this document, 256 radiological scannings of the body are carried out by turning the source and the detector 256 times around the body perpendicularly to the sectional plane whose image it is desired to produce. The detector comprises 256 cells, and a variation in intensity of the X-rays between the source and the detector is measured for each scanning, along $p=256^2$ scanning profiles. By means of a suitably programmed computer, the $p=256^2$ values associated with the $p=256^2$ points of the sectional plane are calculated. This calculation is normally performed by an algebraic reconstruction technique (ART). However, the improvement that is advocated here consists in treating first of all only a sub-assembly of the $p=256^2$ scanning profiles, for example a quarter, i.e. 64×256 scanning profiles. These profiles are obtained by averaging by four the p scanning profiles that are actually carried out, or by selecting one in four of these p profiles. The algebraic reconstruction technique is then applied to the values calculated from the sub-group of scanning profiles, to arrive at an image representative of the $256^2$ points of the sectional plane, in other words the highest possible definition of the image according to the detector that is used.

SUMMARY OF THE INVENTION

The early detection of cancer presupposes a considerable gain in definition. However, the length of time the system is used for a specific patient cannot exceed a certain economic threshold. Above all however, increasing the number of profiles increases the overall radiation dose.

However, it is known that the development of a cancerous nodule accelerates when it causes an associated vascularisation, this phenomenon occurring when a critical size is reached, say for example 50 microns. In the conventional procedures the radiation dose and the calculation time are multiplied by 8000 in order to achieve that definition.

This is the reason why the inventor first of all attempted to obtain an increase in the definition and to find a solution that takes into account the increasing calculating power of computers and the much slower progress in X-ray equipment.

To this end, the object of the present invention is a method intended to reduce exposure to radiation or to ultrasonic beams or magnetic pulse beams in an organism, from medical imaging equipment, thanks to a modification of the procedure for processing signals, in order to obtain representative images of values associated with each point or zone of a planar or non-planar surface, which comprises:

producing a first image by known methods in order to obtain as precise an estimation as possible of the value associated with each point or zone in a representation of the image, via a rectangular matrix, by evaluating by interpolation values between two points or by distributing the value of a zone into micro-zones obtained by splitting up the zone, so as to arrive at an amplified matrix starting from the initial matrix, thereby giving a more accurate image of the initial image, measuring precisely, by physical scannings along crossed series of scannings exploring the examined area, the variation between the two ends of each scanning so as to calculate the boundary values of the representative matrix of the investigate image, a boundary value being the sum of the terms of a line or column of the representative matrix, adjusting the value of each term and thus of each value associated with a point of the investigated image by using an adjustment involving the method of least squares and taking into account constraints relating to the boundaries, so as to obtain a finer resolution of the image.

Preferably the value of each term is adjusted by using the following formula:

$$Cij = Bij + \left(\frac{1}{n}\right) * \left(\rho j - \sum_{1}^{n} Bij\right) + \left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

where, in this formula,
Cij is the sought value
Bij is the initially estimated value
(n) is the number of lines of the rectangle matrix
(m) is the number of columns of the rectangle matrix $$\sum_{i=1}^{n} Cij = \rho j$$

for all the values of i, the constraint of the column j, $$\sum_{j=1}^{m} Cij = ci$$

for all the values of j, the constraint of the line i,
and applying to the same set of data, split physically in a different way each time, the same method several times in order to obtain a series of evaluations of the value associated with each zone, so as to obtain the mean value of the measurements and estimate a standard deviation.

Each of the terms Bij is evaluated from a set of physical scannings spaced so as to produce a reduced matrix representative of the image, by distributing each of the terms of the reduced matrix in a square in which the number of lines and columns is equal to k, regarded as the coefficient of amplification of the initial matrix, so as to obtain the reference matrix, amplified k times, and resulting in a more accurate first image, intended to be adjusted.

The invention also relates to an apparatus for implementing a method according to the invention, characterised in that an X-ray, infra-red light or ultrasound beam is displaced step by step in a linear manner by means of a guidance system using piezoelectric actuators, so as to obtain coefficients relating to each profile corresponding to a given step in order to produce a set of images obtained by means of two series of profiles, such that in each series the profiles are mutually parallel, and that the two series intersect.

Preferably the beam pivots about an axis that itself moves linearly by means of piezoelectric actuators. Multiple detection barriers are provided in order to produce simultaneously a plurality of parallel images capable of being treated individually or in three dimensions. Plates or other supports for X-ray or laser beams, in particular infra-red beams, or for ultrasound or magnetic fields, are also provided, on which the piezoelectric actuators enable the beams to be oriented or displaced, so as to obtain by means of the set of the detectors information relating to the attenuation of each profile produced by a step of the beam. Two groups of beams may be used, one for investigative purposes and the other for treatment. The apparatus may also include perforated blocking plates, which can be screened by means of two crossed networks of displaceable wires or strips so as to disengage one or more blocking means by displacing the plates or strips.

The invention also relates to an apparatus for implementing a method according to the invention, characterised in that a mirror is displaced step by step in a linear manner by means of a guide means and is caused to rotate about a pivotal point by means of piezoelectric actuators, in order to reflect a laser or infra-red beam in order to obtain coefficients relating to each profile corresponding to a given step of the linear displacement of the mirror and to produce a set of images obtained by means of two series of profiles, the profiles in each series being parallel to one another and the two series intercepting one another.

BRIEF DESCRIPTION OF THE DRAWINGS

FIG. 17 is a table corresponding to an initial matrix wherein values of coefficients of attenuation are indicated before expansion;

FIG. 18 is a table wherein the values of the coefficients of attenuation indicated in the table of FIG. 17 are indicated after expansion;

FIG. 19 is a table wherein the values of the coefficients of attenuation after expansion as indicated in the table of FIG. 18 are indicated together with line and column constraints;

FIG. 20 is a table wherein the values of the coefficients of attenuation after expansion, the constraints and the calculations are indicated;

DETAILED DESCRIPTION OF THE PREFERRED EMBODIMENT

Figure 1:
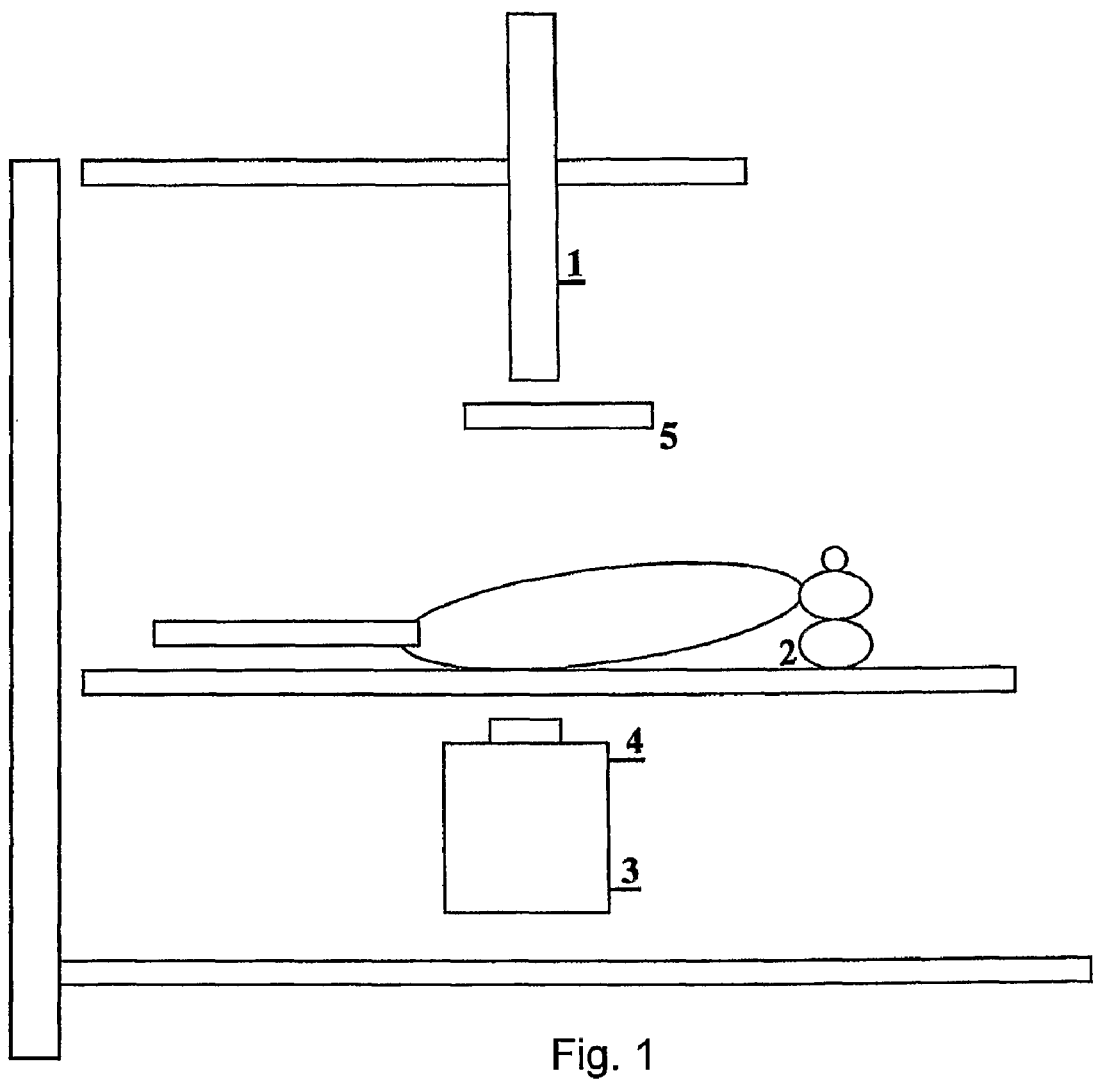
FIG. 1 is a schematic diagram of a first embodiment of an apparatus according to the present invention.

In a preferred embodiment in which a laser or infra-red beam is used, two transparent plates are provided, coated with anti-reflection layers in order to prevent a reflection of the infra-red beam, and mutually parallel in order to limit a refraction of this beam, the object to be examined being arranged between the two plates and resting against one of them serving as support plates.

Thus, the combination of an accurate scanning apparatus together with screens of very small dimensions that can be positioned and switched in an extremely precise manner, and an information processing system providing an acceptable evaluation of the values of the coefficient of attenuation of each elementary micro-zone, enables the number of beam pulses and thus the number of profiles to be recorded to be reduced by a considerable factor, while at the same time increasing the definition from 1 mm to 10 or 20 microns without involving a prohibitive level of irradiation.

In fact, for a 1000×1000 image matrix the resolution by the standard method requires one million profiles. By the method disclosed hereinafter it is possible first of all to obtain an image corresponding to a standard image corresponding to a 20×20 matrix and then to derive from this a simply extrapolated second image in order to arrive at a 1000×1000 image, and then to rescan the investigated organism along two axes involving only 2000 profiles so as to obtain a satisfactory estimate of the coefficient of attenuation of each of one million points. According to this method it is sufficient to produce 400 profiles in a first stage, then 2000, i.e. a total of 2400 profiles, which corresponds to a 99.76% reduction of the necessary number of profiles.

The level of irradiation is in this case divided by 417, this improvement being even more significant for important areas of investigation.

To examine a 20×20 cm zone with a definition of 1 mm, as is currently carried out, the coefficients of attenuation relating to 200×200 points, i.e. 40 000 points, are obtained, which requires the production of 40 000 profiles. If it is desired to obtain a definition of 10 microns, it is necessary to have available values of the coefficients of attenuation of a number of points 10 000 times greater, i.e. 400 million points, and to subject the patient to a lethal level of irradiation, quite apart from the fact that this therefore involves delays and virtually prohibitive costs, regardless of whether the echograph or magnetic resonance imaging method is used.

In the process described here, it is necessary to produce 40 000 profiles in order to obtain a low definition image, followed by 40 000 supplementary profiles for the high definition crossed scanning, i.e. a total of 80 000 profiles instead of 400 million profiles, in other words a division by 5 000 in the number of profiles and associated irradiation.

However, the problem still remains of how to process the signal and the values associated therewith.

The inventor has thus been forced to perfect methods for processing the signal and associated information, so as to solve the particular problem concerning the evaluation of the terms of a rectangular matrix, representative of the sectional profiles of a specific area investigated by a scanner when approximate estimates relating to each term are available, but precise information is available concerning the sum of each line or column of the matrix.

Several methods have been perfected and investigated in order to solve the problem encountered in various imaging contexts. Research has led to an original method, which provides a considerable simplification in the calculation process with a view to obtaining the desired image, represented by a rectangular matrix.

The set of the attenuation coefficients of the points of any area situated in an examination plane, or on a surface, may in fact be represented by such a matrix.

In the case of medical imaging this enables the number of profiles to be produced to be reduced.

This method, which will now be described hereinafter, in fact enables matrices of larger size to be produced by a distribution or an extrapolation of the values of each term or zone of a low-definition initial matrix in order to obtain estimated values in micro-zones, obtained by slicing each term or zone of the initial matrix.

An expanded matrix is thus obtained.

This expanded matrix is then adjusted by a calculation process enabling each term to be reliably evaluated if it is desired to obtain the values of the boundary elements, a boundary element being the sum of the terms of a line or column.

In this case one may go for example from a 5×4 matrix containing 20 terms to a 25×20 matrix containing 500 terms, and then calculate each of the terms by the described method.

This, then, involves expansion and adjustment of the initial matrix representative of the signals obtained, so as to obtain the various profiles.

The description of the adjustment method is described below. This method plays a special role in the calculation carried out after, where appropriate, obtaining a large dimension matrix from a smaller initial matrix.

The following description thus relates to the adjustment calculation method per se according to the invention. This method plays an important role in the processing of the signals obtained from the measurement, by the radiographic detectors, of the intensity or of the residual value of the primary beam produced by the X-ray apparatus, after the beam has passed through the organism being investigated.

If it is desired to process a matrix having dimensions of n lines and m columns, let Bij be the estimated value at the line i and at the column j, let Cij be the most probable value of the corresponding term of the matrix, let ρj be the sum of the terms of the column j, let ci be the sum of the terms of the line i.

The estimate of Bij is obtained either by the matrix expansion process, or by any other method providing such an estimate, in particular using linear or polynomial adjustment techniques.

In the present case the solution of the values of Cij will be sought, taking into account the constraints of lines and columns, that is to say the minimum of the following function is sought:

$\Sigma(Cij-Bij)^2$ for all values of i and j subject to the constraints:

$\Sigma Cij = \rho j$ for all the values of j $\Sigma Cij = ci$ for all the values of i The search for a minimum of the functions subject to constraints will be carried out using the method of Lagrange multipliers, the Lagrangian being written:

$$L = -\sum ij(Cij - Bij)^2 + \sum_{j=1}^{m} \lambda j \left( \sum_{i=1}^{n} (Cij - \rho j) \right) + \sum_{i=1}^{n} \mu i \left( \sum_{j=1}^{m} (Cij - ci) \right)$$

This function is composed of two parts, namely a first part that does not have a left-hand character, and a second part that is a set of linear relations.

The Lagrangian can thus be derived for the variables Cij and λj and μi, Lagrange multipliers associated with the line and column constraints (we have in fact two sets of constraints, namely the line constraints and the column constraints).

Under these conditions we are able to obtain a set of linear relations relating to the Cij by differentiating the Lagrangian, and a set of relation values relating to the constraint values, which is written:

By specifying that dL/dCij denotes a partial derivative of the function L for the variable Cij.

$$dL/dCij = -2(Cij - Bij) + \lambda j + \mu i = 0 \qquad 1$$

and the constraints, for all j, respectively all i $$\left. \begin{array}{l} \sum_{i=1}^{n} Cij = \rho j, \\ \sum_{j=1}^{m} Cij = ci, \end{array} \right\} 2$$

$$1 \Leftrightarrow Cij = Bij + (\lambda j + \mu i)/2$$

The set of n×m relations corresponding to the partial derivatives plus the n+m constraint relations is linear and allows only one solution corresponding to the nm+n+m variables.

If for example we wish to process a matrix where n, the number of lines, is equal to 25, and m, the number of columns, is equal to 30, then the solution by linear algebra consists in processing:

750 Cij variables 25 variables corresponding to the line multipliers, the $\mu i$ 30 variables corresponding to the column multipliers, the $\lambda j$.

A first objective is already achieved since only 55 profiles have to be obtained, instead of 750.

We have in total 750 relationships corresponding to the partial derivatives and 55 relationships corresponding to the constraints, for 805 variables. The solution of this problem by employing matrix calculus is the most obvious solution, but involves very tedious calculations, which are slightly more awkward than those involved in conventional methods. The aim of the inventor was first of all rapidly to improve the calculation processes, but over and above his essential objective, namely limiting the irradiation dose during an examination, he has continued to try and improve the calculation time.

The following is obtained by combining the relationships 1 and 2:

and 2:

$$\sum_{i=1}^{n} Bij + \frac{n}{2} * \lambda j + \left(\sum_{i=1}^{n} \mu i / 2\right) = \rho j$$

$$\sum_{i=1}^{m} Bij + \frac{m}{2} * \mu i + \left(\sum_{j=1}^{m} \lambda j / 2\right) = ci$$

One may deduce from these relationships:

$$\lambda j = \left(\frac{1}{n}\right) * \left(2 * \left(\rho j - \sum_{i=1}^{n} Bij\right) - \sum_{i=1}^{n} \mu i\right)$$

$$\mu i = \left(\frac{1}{m}\right) * \left(2\left(ci - \sum_{j=1}^{m} Bij\right) - \sum_{j=1}^{m} \lambda j\right)$$

Under these conditions, by substituting for example the value of $\lambda j$ in $\mu i$, we obtain, for all j $$\lambda j = \left(\frac{2}{n}\right) * \left(\left(\rho j - \sum_{i=1}^{n} Bij\right) - \sum_{i=1}^{n} \mu i\right)$$

For all $i$ $$\mu i = = \left(\frac{1}{n}\right)\left(\sum_{i=1}^{n} \mu i\right) + \left(\frac{2}{m}\right)\left(ci - \sum_{j=1}^{m} Bij - \left(\frac{1}{n}\right) * \sum_{j=1}^{m} \rho j + \sum ijBij * \left(\frac{1}{n}\right)\right)$$

If one defines that $\mu^- = (1/n)\Sigma(i=1 \text{ to } n)\ \mu i$ is the mean of the multipliers associated with the constraint of the lines, we arrive at the two following relationships:

for all $j$ $$\lambda j = \left(\frac{2}{n}\right) * \left(\rho j - \sum_{i=1}^{n} Bi\right) - \mu^-$$

for all $i$ $$\mu i = \mu^- + \left(\frac{2}{m}\right) * \left(ci - \sum_{j=1}^{m} Bij - \left(\frac{1}{n}\right) * \left(\sum_{j=1}^{m} \rho j - \sum ijBij\right)\right)$$

-continued

In fact:

$$\frac{1}{m}\sum_{1}^{m} * \sum_{1}^{n} \mu i \text{ is equal to } \mu^-$$

Under these conditions, and by substituting in the relationship:

Cij=Bij+(½)*($\lambda$j+$\mu$i) we arrive at the algebraic relationship.

This adjustment formula allows us to deduce the matrix of the Cij from the matrix of the Bij by term-by-term calculation $$Cij = Bij + \left(\frac{1}{n}\right) * \left(\rho j - \sum_{1}^{n} Bij\right) +$$

$$\left(\frac{1}{m}\right) * \left(ci - \sum_{j=1}^{m} Bij\right) - \left(\frac{1}{nm}\right) * \left(\sum_{j=1}^{m} \rho j - \sum ijBij\right)$$

The inventor has thus succeeded in a totally surprising manner in carrying out an algebraic-type calculation that does not require the use of matrix calculus.

The algebraic method allows the partial treatment of the reference matrix, which in many cases may be sufficient.

The numerical validation of this method of processing signals and establishing definition values of the sought-after image in a medical context is described hereinafter.

Example of Application of the Method to a Reduced Model

Let us consider a matrix of n lines and m columns in which n=3, m=4:

Initial Matrix

|   | 1 | 2 | 3 | 4 | Σ lines | C |
|---|---|---|---|---|---------|---|
| 1 | 22 | 24 | 18 | 16 | 80 | 78 |
| 2 | 24 | 22 | 18 | 20 | 84 | 85 |
| 3 | 26 | 20 | 22 | 24 | 92 | 93 |
| Σ columns | 72 | 66 | 58 | 60 | 256 | |
| P | 70 | 67 | 59 | 60 | | 256 |

In this matrix the estimated values are entered in the three lines and in the four columns, and the line constraints are entered in the column C.

The column constraints are entered in the last line P.

The application of the above formula is simplified since the total of the column (or line) constraints is equal to the sum of the terms and leads to:

Equilibrium After Calculations

|   | 1 | 2 | 3 | 4 | Σ 2 | C | Δ |
|---|---|---|---|---|-----|---|---|
| 1 | 20.83333 | 23.83333 | 17.8333 | 15.5 | 78 | 78 | 0 |
| 2 | 23.5833 | 22.58333 | 18.5833 | 20.25 | 85 | 85 | 0 |
| 3 | 25.5833 | 20.5333 | 22.583 | 24.25 | 93 | 93 | 0 |
| Σ 2 | 70 | 67 | 59 | 60 | 256 | | |
| P | 70 | 67 | 59 | 60 | | | |
| Δ | 0 | 0 | 0 | 0 | | | |

It may be checked, by taking calculations performed on a simple calculator, that the value of the vertically or horizontally summated terms not only satisfies the constraints but also leads to the desired results.

Equilibration Using the Method of Linear Algebra

This method expresses directly the linear relationships between the variables Cij and Bij, and the variables $\lambda j$ and $\mu i$.

The conventional method for solving a linear system involves inversion of the matrix of the coefficients of the relationships between the variables and the multiplication, by this inverse matrix, of the vector expressing the second terms of the relationships.

a) There are 12 relationships between the variables resulting from the expression of the partial derivatives of the LAGRANGIAN of the form:

$$Cij - \lambda j/2 - \mu i/2 = Bij$$

b) There exist 4 constraint relationships relating to the columns and 3 constraint relationships relating to the lines, of the form:

$$\sum_{i=1}^{m} Cij = \rho j$$

$$\sum_{i=1}^{n} Cij = ci$$

The conventional method then requires the inversion of a matrix of size equal to n*m+n+m, i.e. in our case 19×19, the calculation time for which is clearly far too high.

The Two-Stage Analysis Corresponding to 6 Sequences

A) Matrix Expansion

This takes place in the following order

1. Creation of an initial matrix, representing a double series of crossed profiles corresponding to the elementary coefficients of attenuation of a tomodensitometric investigation; we shall take for example Table No. 1 <<Initial matrix>>.

2. Establishment of a structure table, see in the Annex Table No. 2 entitled <<BEFORE EXPANSION>>, FIG. 17.

3. Inscription in the cases close to each of the values divided by 25, which leads to Table No. 3 <<AFTER EXPANSION>>, FIG. 18.

B) The Adjustment is Carried Out as Follows

4. Inscription of the line and column constraints, which leads to Table No. 4 <<EXPANSION+CONSTRAINTS>>, FIG. 19, in which the sums of the lines and columns, and the corresponding constraints are shown. Each constraint results from the physical measurement of the total attenuation value of a profile obtained by reading the value displayed on the end detector of the profile, according to a particular scanning.

5. Calculations of the values by the formula given hereinbefore, which leads to Table No. 5 <<EXPANSION+CONSTRAINTS+CALCULATIONS>>, FIG. 20.

Figure 21:
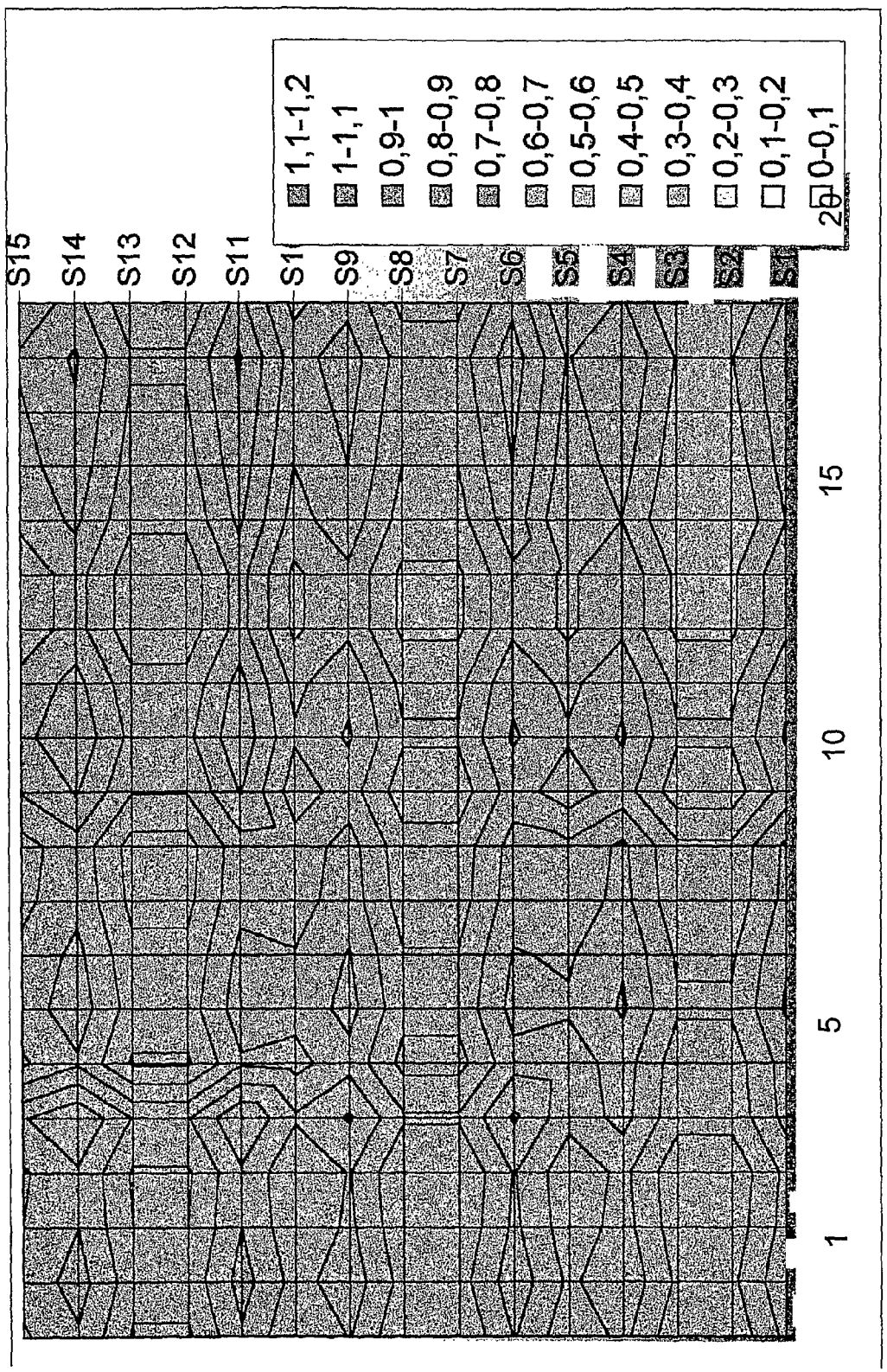
FIG. 21 is a representation of iso-attenuation lines of the values of the coefficients of attenuation calculated as indicated in the table of FIG. 20.

6. Table No. 5 may then be represented, as regards the values of the Cij, by a coloured and graded image, constituting Table No. 6-1, FIG. 21.

The medical specialist has thus achieved the desired result of a medically usable image having a better definition by means of a limited number of operations, and thus a lower dose of radiation than is required by existing methods.

In fact, the whole area in a plane or on a surface leads to the creation of a rectangular matrix, this matrix resulting simply from the formation of two series of profiles which are mutually parallel in each series, each series being perpendicular or not to the other. It may also be produced by information obtained in polar co-ordinates, with series of profiles passing through a given pole and possibly intersecting with profiles obtained from another pole.

It will be recalled that it is always possible to process only one part of the reference area without any problem.

In fact, it is even possible to restrict the calculation to one or more image zones (assuming that the method of calculation is the same).

The stages of the method are then as follows:

a) An examination is carried out with a scanning of conventional definition, for example 1 mm.

b) An appropriate image is obtained.

c) An area of fine investigation is defined.

d) A high-definition scanning is then carried out with a suitable device, involving specific displacement means.

e) The information from the chosen area is then processed, which involves the following:

e.1) Estimation of the attenuation values of the micro-zones resulting from the division of the elementary zones in an appropriate manner, starting from a reference image obtained by an examination using a scanning procedure with conventional definition, e.2) Calculation of the values of terms of the matrix corresponding to the specific area, by the adjustment method described hereinbefore, on the basis of the high-definition scanning, e.3) If necessary the process may be repeated, based on a total or partial change of the scale of the sectioning, or of the investigated zone, or if appropriate the scanning may be repeated at different angles of the same zone so as to obtain several values of the attenuation of each micro-zone, the mean value of which provides an improved valuation and may be associated with a standard deviation.

f) The creation of a database of the attenuation values of each micro-zone in the various phases of the investigation.

g) The partial or complete editing of the results and the visualisation resulting therefrom in two or three dimensions, in black, grey and white, or coloured.

A focussed treatment may be carried out if necessary, using the same fine scanning techniques and where appropriate the investigation apparatus, if the required power has to be increased, which is the case. It is then possible to use am X-ray laser beam (or any beam of small cross-section), which will be used in several repetitions at an appropriate amplification level so as to combine investigation and treatment while reducing the risk of irradiating irrelevant organs.

In order to obtain the information necessary for the subsequent treatment, two methods may be adopted:

1—With Two Combined Apparatuses a) A tomodensitometric analysis may in fact be carried out with an existing scanner comprising a ring, which allows a sufficient number of scannings in order to obtain a 1 mm definition of the image. The information is stored in the memory of the information system, following which the value of the coefficients of attenuation of each micro-zone resulting from systematically dividing up each zone is obtained, and restricting in a precise way the supplementary investigation.

b) A high-definition scanning is then carried out in a second, specialised apparatus so as to obtain in a defined area the value of the coefficients of attenuation along rays of the beam much closer together. The configuration of this second apparatus may be identical to that of the first, though the scannings may be restricted to smaller angular zones, the angle then being a function of the number of steps to be carried out, in order to obtain a set of sufficient cross measurements. The second apparatus may be more simply rectangular in order physically to materialise a matrix. In this case two beams are displaced perpendicularly so as to create directly a matrix rectangle, which will be subjected to the mathematical correction treatment, the nature of which has already been described.

c) The problem is also one of adjustment so that the zones can be treated by exact superpositioning. Two solutions may then be employed:

c.1) A solution involving analysis of the images obtained by the two devices, both of which are rotatable, using a software enabling a precise comparison to be made of the coefficients of attenuation in each image so as to allow a superpositioning of the images obtained, on the same scale.

c.2) Another solution involving positioning for example physical reference marks, such as a particle of lead or other materials having properties that are easy to detect, on the skin. These particles are the equivalent of topographical boundaries.

2—With an Integrated Device

This device allows a double scanning operation, for example as follows:

a beam displacement scanning with a step of the order of 1 mm, in order to obtain an image such as is produced by an existing type of scanner, sequentially (or simultaneously) a scanning involving a very small displacement of the beam (with a step of ¹/₁₀ or ¹/₁₀₀ of 1 mm) so as to produce on the same image the two types of information based on the same topography.

A device described hereinafter will allow one and/or the other of the scanning methods to be used at the expense of a certain degree of complication in the implementation of the two scannings, especially if they are carried out simultaneously.

One will be able in this case also to complete the adjustment of the images by physical reference marks, by placing on the skin or even in the organism materials having a very high absorption.

In fact, molecules that are able to concentrate in tumours or in the associated vascularisation zones may be injected.

In the case of the integrated device it should be sufficient to arrange a stable rectangular physical system supporting the blocking and detection plates and associated with two mobile beams, which move perpendicularly and are inclined independently with respect to one another so that each can cover a large zone of for example 90° inclination.

Alternatively, if displacements occur while maintaining a given angular position, the combination of the displacements can be adjusted according to protocols suitable to the case being treated. The final objective is to have available two sets of data:

A large scanning reference matrix enabling each zone to be identified,

A matrix obtained from information produced by fine scanning, capable of being handled by the mathematical methods disclosed at the start of the description of the process, in order to evaluate the values of the coefficients of attenuation in each micro-zone.

Diagram No. 1, entitled <<Overall arrangement>> shows an example of implementation. In this diagram, FIG. 1, the particle or beam accelerator 1 can move. The positioning plate 2 is displaceable as regards height and can move horizontally 9. The absorption plate 3 is composed of heavy materials to absorb the radiation. The supporting plate for the detection bars 4 supports a set of bars enabling the coefficients of attenuation to be read in the absence or presence of the body or object to be examined. The blocking device 5 consists of a set of orifices with adjustable positions and openings.

This diagram represents a cross-section of the overall physical system. The table 2 on which the patient rests is placed inside a frame. The vertical beam 1 passes through a plate of blocking devices 5, then through the patient followed by the table, to reach the plate 4 supporting the detectors, which is connected to the information processing device.

We have chosen to illustrate the new case of a rectangular frame associated with at least two inclinable and displaceable beams.

Figure 2:
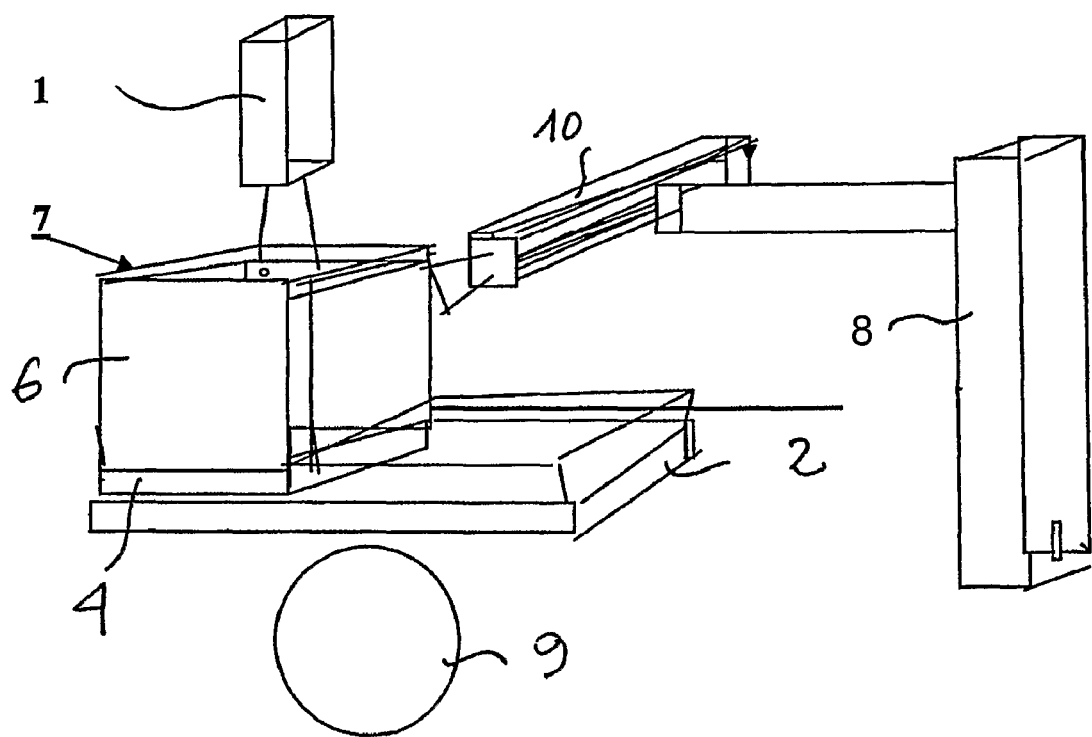
FIG. 2 is a perspective view of a variant of the first embodiment illustrated by FIG. 1.

Diagram No. 2, entitled <<Perspective view of beams and blocking devices>> is a projection of the arrangement showing the vertical and horizontal scannings seen in perspective, in a variant in which the frame is placed on the table and the patient lies on a mattress, which can be introduced into the frame. In this diagram, FIG. 2, 1 denotes a vertical beam, 10 a horizontal beam, 2 a positioning table, 8 a bracket supporting the horizontal beam device, 4 a horizontal detection plate, 6 a vertical detection plate, and 7 a horizontal blocking grid.

In this variant the beam does not pass through the table, the object of this arrangement being to eliminate the problem of the said table in the processing of the information.

It is of course possible to use beams of normal power so as to restrict the risks from radiation. In this case the treatment will assume that two types of beams, or an X-ray laser operating at several levels of amplification, are available at the same site.

In order for the organism to receive the beam in a precise manner, a lead plate in which a window is open is placed in the trajectory, the dimensions and sectioning details depending on each envisaged analysis protocol or treatment.

Figure 10:
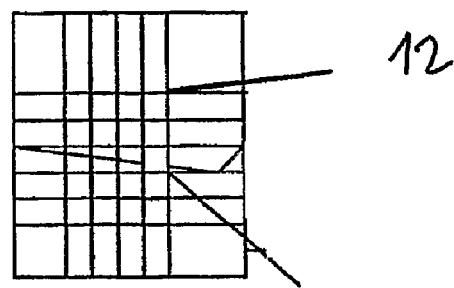
FIG. 10 is a schematic view of a grid of two superposed sets of wires.

In the case of our system an extra plate containing very small orifices of one to two hundredths of a millimeter is installed; these orifices may be blocked preferably by the movement of very fine wires. A grid of two superposed sets of wires, i.e. horizontal wires 12 and vertical wires 13, FIG. 10, is thus formed, which intersect at a right angle. These two sets simultaneously block the orifices. For a definition of 1 mm, the wires are replaced by strips of width 0.8 to 1 mm, see diagram 5 <<blocking system>>, FIGS. 10 to 13.

Figure 11:
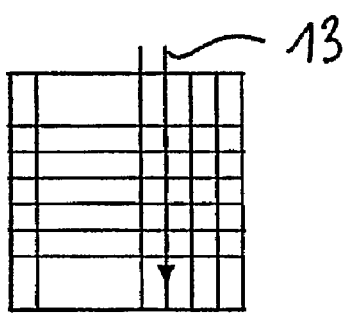
FIG. 11 is a schematic view of horizontally moved wires of the grid shown by FIG. 10.
Figure 12:
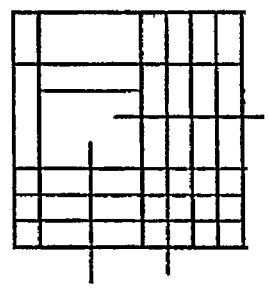
FIG. 12 is a schematic view of vertically moved wires of the grid shown by FIG. 10.
Figure 13:
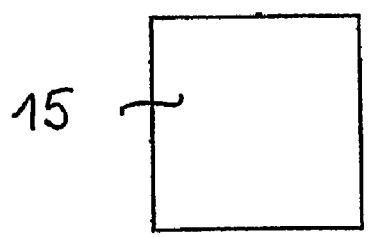
FIG. 13 is a schematic view of a control box controlling the movement of the wires of the grid shown by FIG. 10.

The displacement of two wires along the X axis and Y axis unblocks a single orifice; the simultaneous displacements of two sub-sets unblock a rectangular area (see diagram 5, FIG. 10). FIG. 11 shows wires 13 moved horizontally. FIG. 12 shows an opening 14 after a vertical movement of the wires 13.

These displacements are achieved in a precise manner by using piezoelectric actuators. The unblocking of a precise area is effected for a very short time, so as to expose for one or a few milliseconds the micro-zones to be examined or treated. A control box 15 controls the movements of the wires, FIG. 13.

Figure 3:
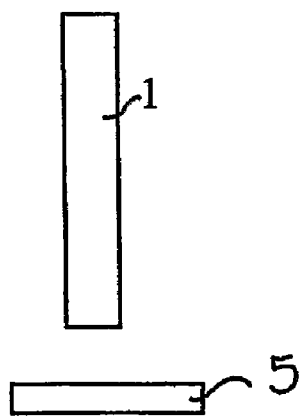
FIG. 3 is a schematic view of a blocking device of the beam of the apparatus shown by FIG. 1 or 2.
Figure 4:
FIGS. 4 to 8 are schematic views of various forms of blocking devices.
Figure 5:
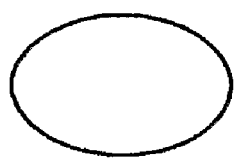
Figure 6:
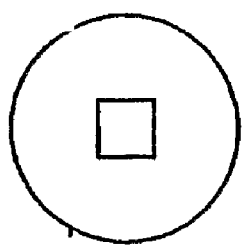
Figure 7:
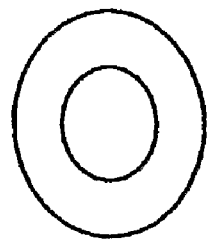
Figure 8:

Reference should also be made to diagram No. 3, entitled <<Beam and blockage>>. In this diagram, FIG. 3, the blocking devices 5 of the beam 1 consist of a series of inspection holes operating simultaneously or independently, which are movable and are grouped in blocks. Various forms of blocking devices are shown in FIGS. 4 to 8. FIG. 8 shows more specifically a slit of variable cross-section.

In order to avoid the difficulties inherent in such procedures, it will be preferable to use a double function positioning and observation laser, similar to those used for distance and topographical positioning measurements.

The arrangement and the description are given on diagram No. 4 entitled <<Reference laser>>. Such a laser can be used when a transparent portion of the organism such as the eye is being treated, or if it is desired to examine a surface such as the skin or an internal organ during a surgical intervention.

Figure 9:
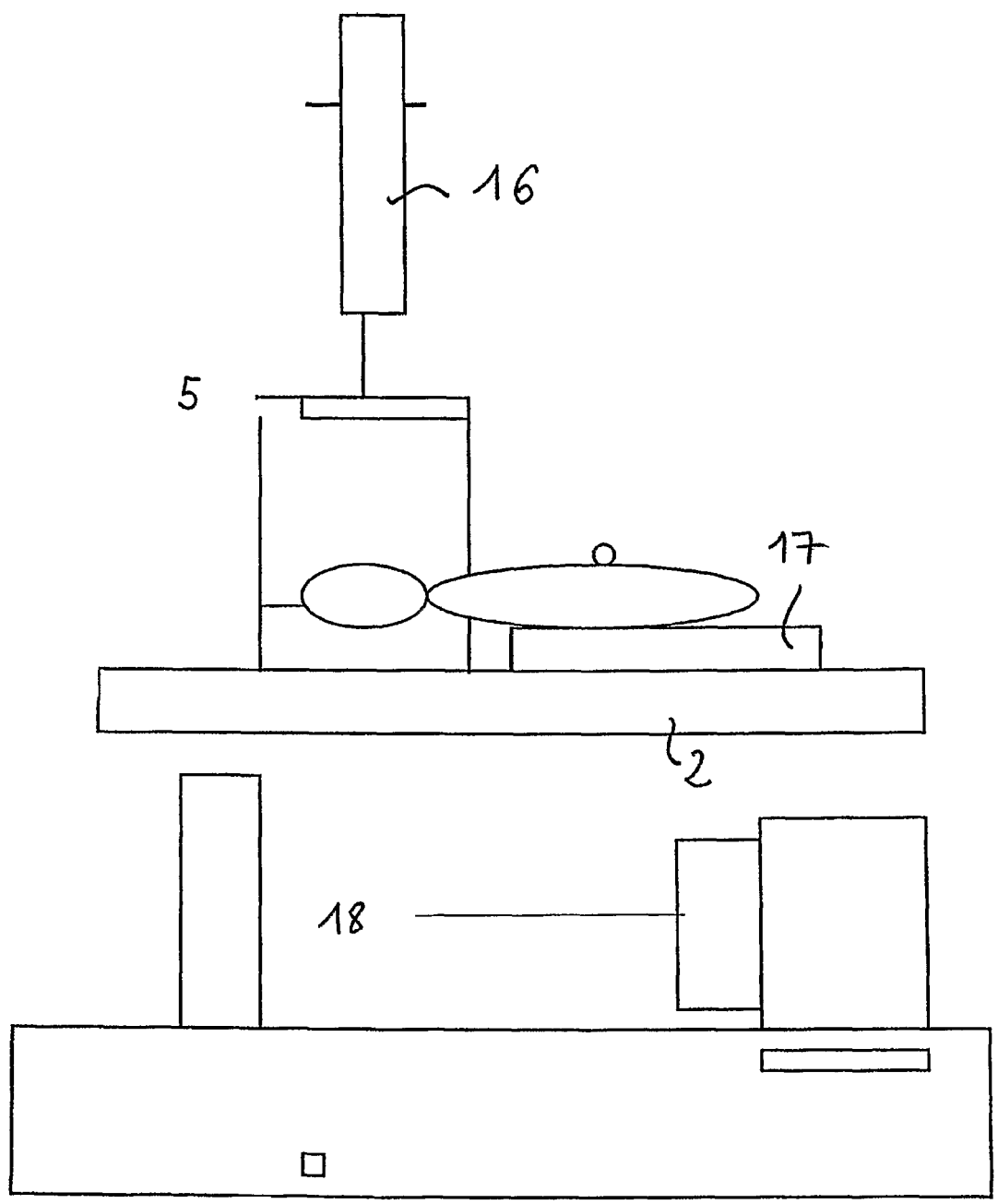
FIG. 9 is a schematic view of a variant of the apparatus shown by FIG. 1, wherein a double function positioning and observation laser is used.

The use of blocking and detection plates and real, very fast-acting grids is intended to permit a framing operation of the area to be examined without physically displacing the object or the patient. In the diagram 4, FIG. 9, the reference laser 16 occupies the exact position of the X-ray beam. The frame carrying the blocking system 5 is in the trajectory of the rays. The supporting table 2 also supports the blocking frame and the detection frame. The supporting mattress 17 is adjusted to the height of the detection frame. The electrical switchdiagram 18 connects all the information to the information processing system.

Diagram No. 6 entitled <<Analysis of the scanning>> shows the scanning method used.

Figure 14:
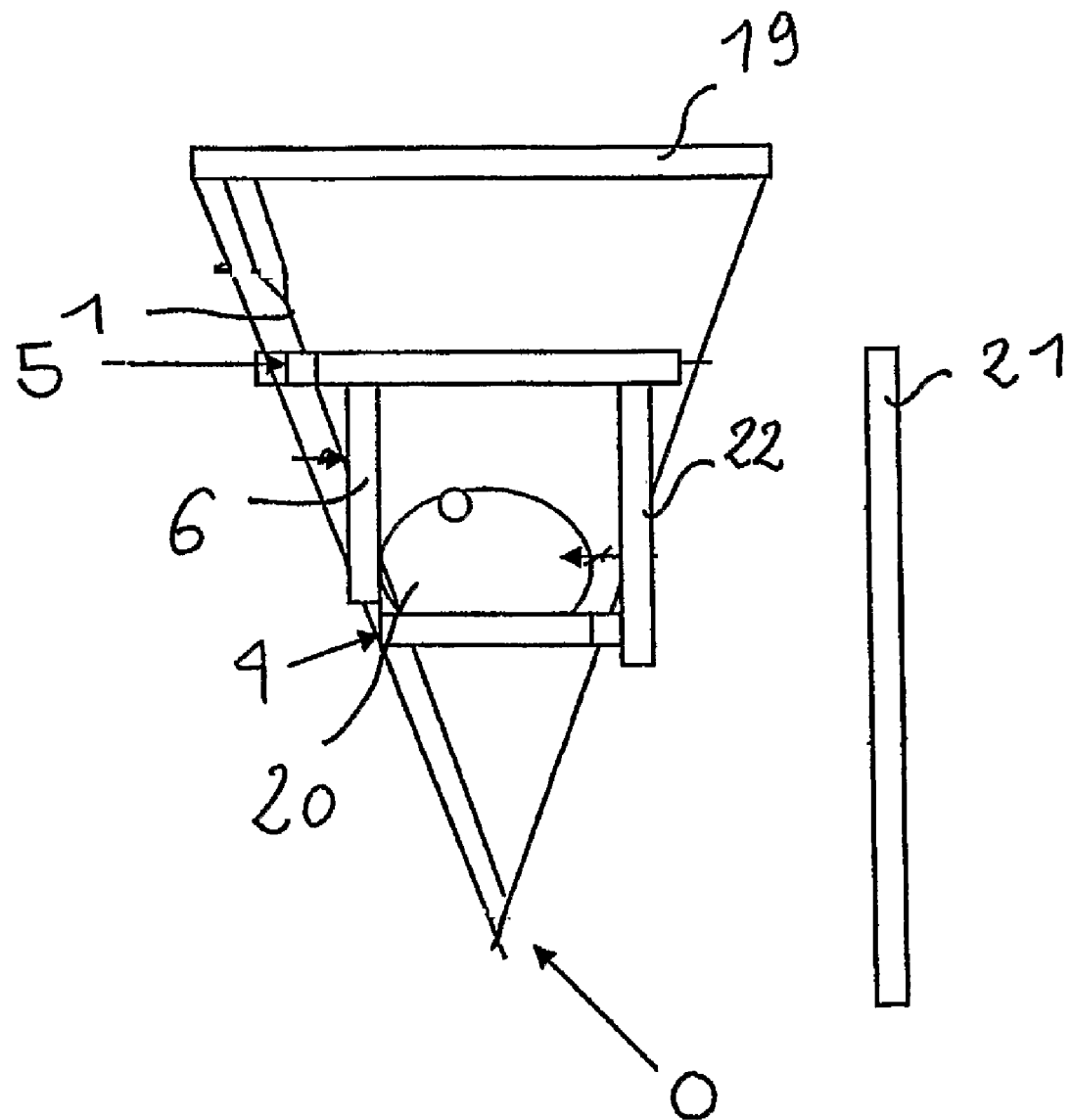
FIG. 14 is a schematic view of an apparatus according to a second embodiment of the present invention.

In FIG. 14 the beam 1 moves along a scanning plate 19 and executes a step by step movement. In the case of the conventional method, at each step it is inclined progressively so that the successive beams converge towards a central point O. Each scanning allows the beam to pass through the blocking plate 5, then the zone to be examined 20, and finally to reach the detector 4 in a zone aligned in the axis defined by the position of the point of impact of the beam with the plate and by the angle of shot.

The number of profiles to be obtained should be equal to the number of elementary examination points, so as to determine with certainty the coefficient of attenuation of each zone.

A good approximation may be obtained by a sequence of fine scannings such that a sufficient number of estimates of each micro-zone are obtained in order to calculate a suitable mean value and standard deviation for each term of the expanded matrix.

In the case of fine scanning the inclination remains constant for the two beams 1 and 10, or for the same beam if, as in FIG. 14, the suporting plates 19, 21 of the beam, of the blocking device 5, 22 and of the detector 4, 6 move from the horizontal position 19, 5, 4 to the vertical position 21, 22, 6 by performing a displacement in order to carry out two series of analysis enabling the two scannings to overlap over the whole zone to be examined.

The system thus functions in four stages for the fine scanning.

1. Defining the area to be examined, for example 4×6 mm,
2. Specifying the position of this area by defining the X co-ordinates and Y co-ordinates of the four corners,
3. Actuating the appropriate beam or particle accelerator for the treatment, or X-rays for the analysis, or X-ray laser operating at several levels, a low level for the investigation and a higher level for the treatment,
4. Rapid unblocking by displacement along two axes of co-ordinates of the blocking wires.

The information provided by the detectors is transmitted in real time to the information processing system in the case where the same device is used for the two phases of the operation, which assume:
a scanning with a step of 1 mm for the whole examination followed by a scanning with for example a step of 20 microns.

The first scanning will be carried out by moving and inclining the beam according to a standard protocol, the blocking devices opening in order to allow an examination of pre-defined zones under different standard conditions. For an area of 10×100 cm, 10 000 profiles will be carried out in order to calculate precisely the values of 10 000 points by inversion of a 10 000×10 000 matrix, or under much quicker conditions if it is sufficient to obtain mean values associated with standard deviations, for a series of measurements processed by the adjustment method described hereinbefore. This procedure limits in particular the level of irradiation.

For the second scanning, the two beams will preferably be able to maintain their inclinations and to both move in a limited field so as to permit the examination of for example a rectangular area of size 4×6 mm, involving the generation (for a definition of 20 microns) of a rectangular matrix of 200×300 points per cross-sectional (cutting) plane, i.e. 60 000 points, the numerical treatment of which will remain within acceptable limits, bearing in mind the algorithm already described, while limiting the level of irradiation.

Figure 15:
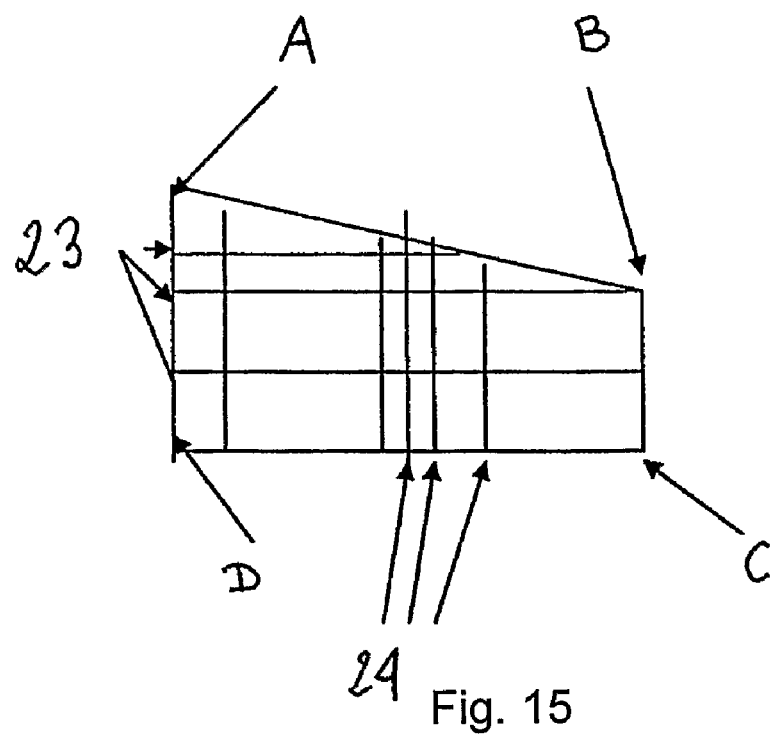
FIG. 15 shows a trapezium with corners A, B, C and D.

Diagram 7 entitled <<Special scanning>> is of particular interest, and shows that it is possible to use a single, for example horizontal, scanning plate 19, and a single detection plane 4, in this case a horizontal plane. FIG. 15 shows a trapezium with corners A, B, C and D. The reference numerals 23 and 24 denote respectively horizontal lines and vertical lines.

Figure 16:
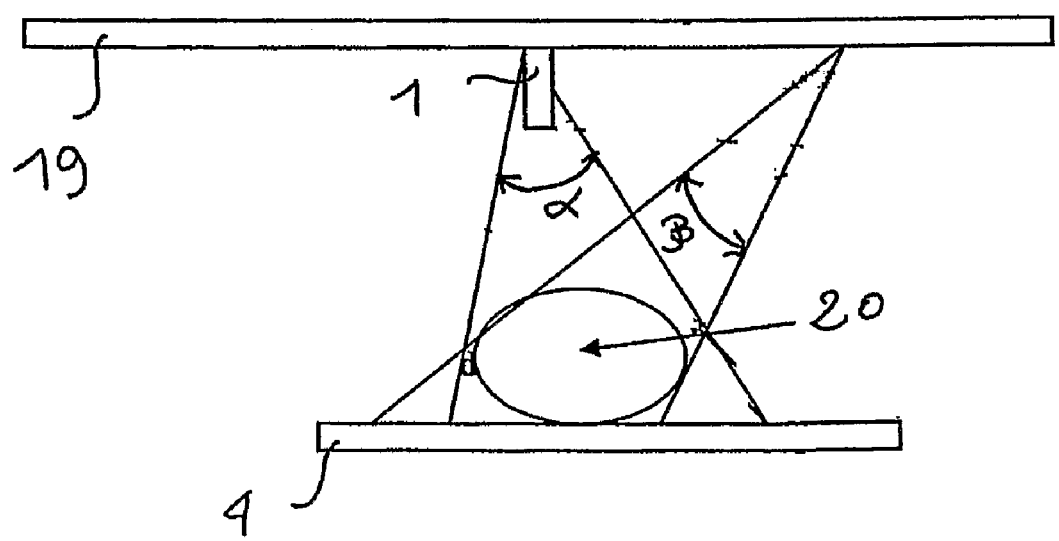
FIG. 16 is a schematic view showing two scannings at two different angles $\alpha$ and $\beta$.

Under these conditions, FIG. 16, the object 20 is scanned in the tomographic plane, for example under two angles $\alpha$ and $\beta$ such that the scannings overlap at a sufficient number of points so as to obtain an evaluation for each point closer than 1 mm, and thereby obtain a precise evaluation.

This procedure will be completed by at least two scannings involving a movement in steps of about 20 microns or involving rotation by a fraction of a degree per step, in order to obtain the necessary data for the processing by the method already described. The angles of the two sets of scanning may or may not be equal to 90°. The complication resulting from the use of non-orthogonal axes of co-ordinates is negligible as regards the calculation.

It will be recalled that the apparatus may comprise an X-RAY LASER beam, in which the rays pass through the object or patient to be examined. After the passage of the beam a detector enables the residual power of the beam to be read in order to measure the coefficient of attenuation during the passage of the beam through the examined object or patient.

This beam passes point by point in front of a set of blocking devices, which may consist of small movable screens arranged opposite orifices of very small cross-section.

It is possible to use a sufficiently large beam so as to cover a set of blocking devices, and affect an equivalent bar of detectors.

If it is accepted that certain natural movements (for example respiration) can displace elements of an organ at a rate of 1 cm per second, and if it is desired to obtain a precision of the image of 10 to 20 microns, the functioning time of the blocking device should be of the order of a millisecond, and the apparatus should produce a series of successive flashes of very short duration.

If therefore the beam has to be produced and interrupted very rapidly (in the case in particular where a light or X-ray laser is used), or if the blocking arrangement has to be altered rapidly, the functioning of the control (electrical or mechanical) for a very short duration comes up against the limits of the electromagnetic systems at the technical level, or of the electronic systems at the cost level.

In European Patent No. 99401358 filed by Norber BEY-RARD, relating to <<a piezoelectric control contactor>>, the inventor describes a control device for a contact circuit-breaker in which the movements are effected by means of a piezoelectric actuator.

The most recent test show:

That the interruption of the current may take place in a time of the order of a millisecond.

That the interruption of the current may, thanks to a suitable electronic circuit, take place when the current passes, for example in the case of alternating current, at the point where the intensity is zero.

Without extrapolation, a control device can be provided comprising:

An alternator (or a modulator) supplying a current of frequency equal for example to 200 or 400 Hz.

An electronic circuit allowing the circuit to operate at the moment of a first passage of the current of zero intensity, and interrupting the circuit during the following passage of current.

Under these conditions the device will be triggered or unblocked for a half-period equal to 1/800 of a second, i.e. 1.25 milliseconds, or 1/400 of a second, i.e. 2.5 milliseconds.

In the device perfected by Norbert BEYRARD and which comprises an electronic control circuit, it is possible to lock and then unlock the electrical circuit so that the functioning period is adjusted in a precise manner, while maintaining the situation that the opening or closing of the circuit takes place at the moment when the intensity of the alternating current (sinusoidal) passes through the point of zero intensity.

It is thus possible to effect the opening and closure of a circuit at a precise moment in time.

If therefore the displacement of the object or zone to be examined takes place at a rate of 1 cm per second, the object or zone will be able to be examined during a period of 1 to 2 milliseconds, corresponding to a displacement of the order of 10 to 20 microns. In order to take account of random variations the beam should have a diameter of 100 microns (which is normally the case for some X-ray lasers).

We are concerned here with an essential point that allows the investigation of a definition of the order of 10 to 20 microns instead of the current value of 1 mm, i.e. a gain in definition of 50 to 100 compared to the current technique.

The economic gain that is thereby obtained may be easily calculated.

Such a cutoff device as described in the aforementioned patent should cost no more than about 10 Euros for a series production possibly involving other items; electronic cutoff for example by means of a thyristor involves a cutoff system whose price is about 100 times higher.

If systems having such a precision are available, the amount of information produced by the detector is multiplied considerably and would rapidly exceed the limits of the software and calculators generally associated with the current scanners.

The calculators associated at the level of the device would have to process a set of linear equations and variables 125 000 times larger for a gain of definition of 50.

We shall consider an object of cross-section 20×20 cm for a zone of 1 mm. We then have to calculate 200×200 coefficients of attenuation per cross-section, i.e. 40 000 points. Despite programming short-cuts, the time and cost of the calculations are still considerable even today.

If the definition is improved by a factor of 50, the speed and thus the power of current calculators has to be multiplied considerably (by the order of 125 000).

If we assume that Moore's law continues to apply in the future, and that the calculating power therefore doubles every 18 months, we would have to wait 25 years for the systems to become operational.

This is why it is necessary to use another method, such as described hereinbefore, in order to accelerate the process.

The calculation process is then as follows:

In a first stage an attempt is made to estimate the coefficients of attenuation of reduced zones.

We shall assume that a limited zone taken from the interior of a cross-section investigated in a conventional manner is examined, and that this zone has for example a size of 4 mm×3 mm. In such a zone we have 12 zones, for which different coefficients of attenuation have been calculated, either conventionally or otherwise.

The value representation of each zone is expressed in Table 1, <<Initial matrix>>, page 2.

Figure 17:
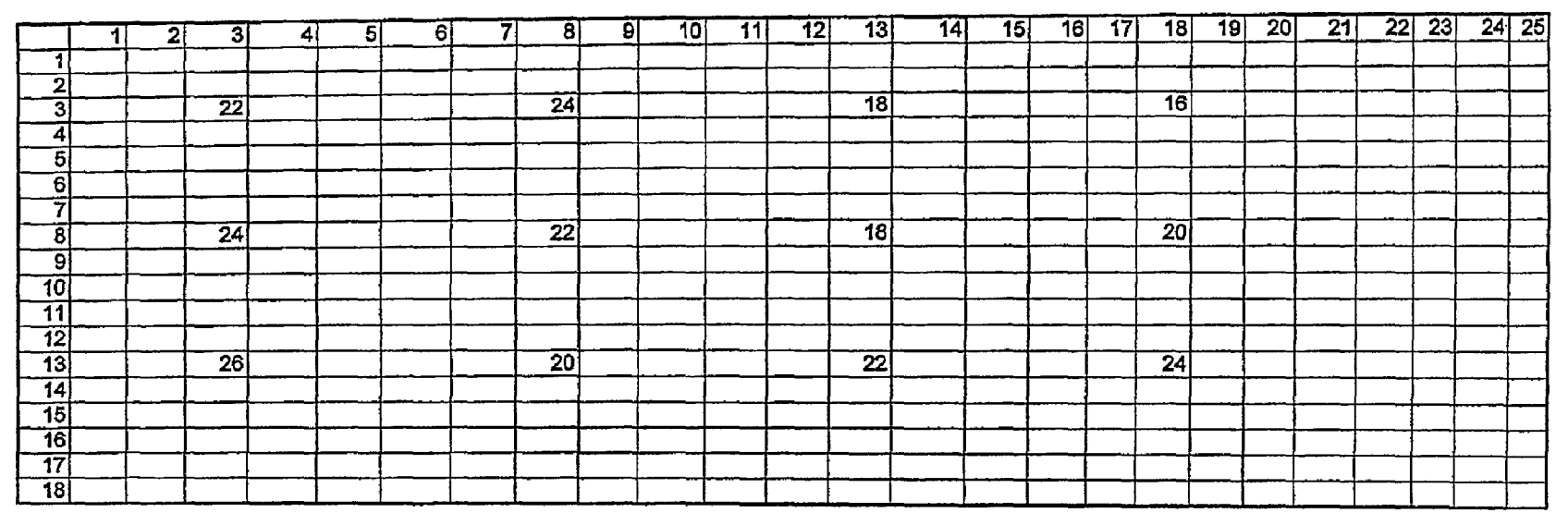

Each zone is then split up into twenty-five (5×5) smaller zones, which is why in the table of FIG. 17 <<BEFORE EXPANSION>>, the value of the coefficient of attenuation appears in the centre of each zone.

The coefficient relating to the expanded initial zone No. 1 is equal to 1/25 of 22, i.e. 0.88, and one can see in the table of FIG. 18 <<Matrix after expansion>> the expanded matrix, which shows the coefficients of attenuation of each microzone after distribution.

The values of the constraints are shown in the table on FIG. 19 <<After expansion+constraints>>, and complete the information shown in the table of FIG. 18.

Figure 20:
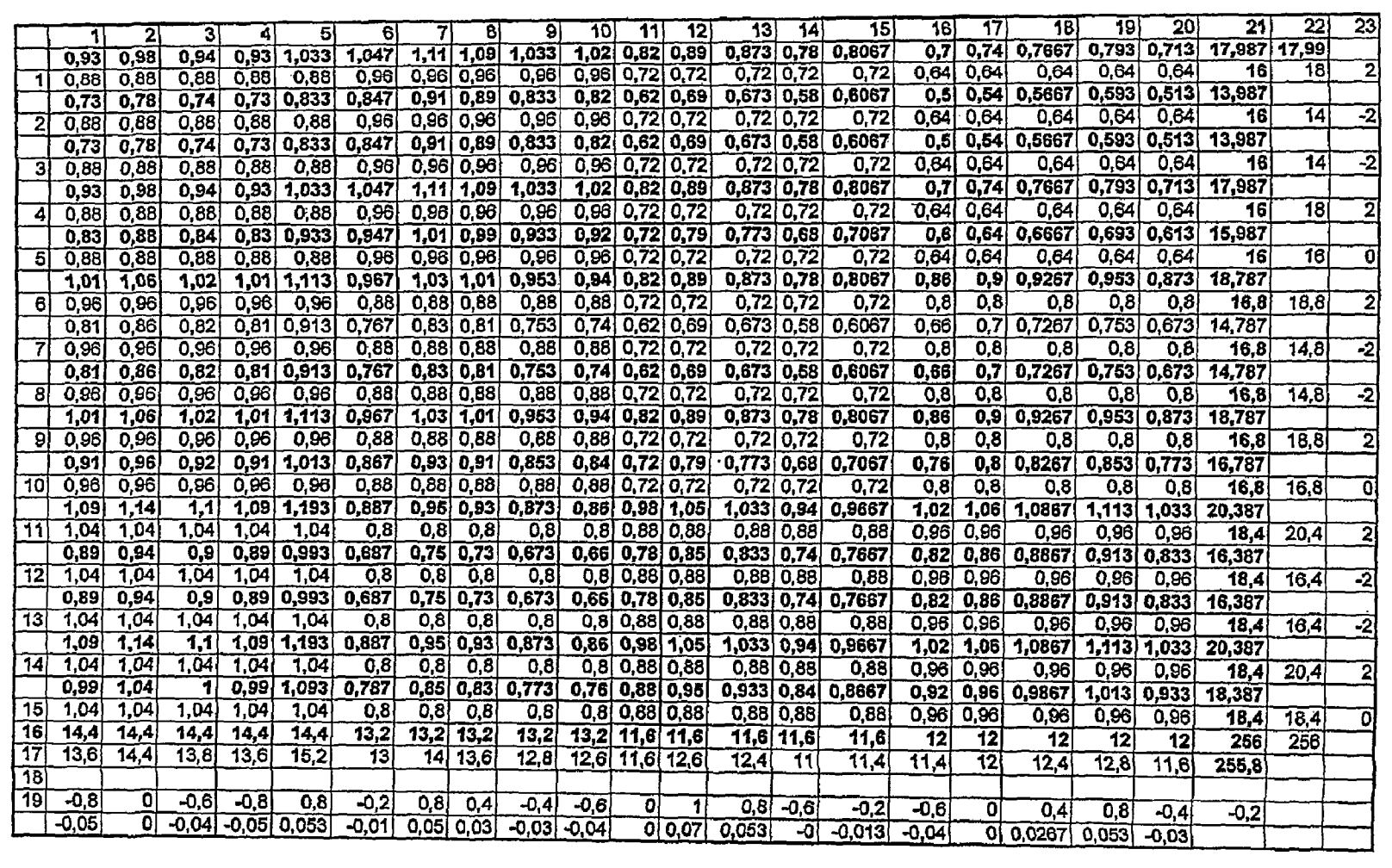

We have tested the adjustment method described above on the basis of the table of FIG. 19, and have checked its operation by preparing the table of FIG. 20 <<Expansion+constraints+calculations>>, which shows that the estimated sum of the coefficients of attenuation is indeed equal to the value of the constraint.

An examination of this table 5 allows us to follow the calculation process:

1. The numbered lines indicate the estimated value of each term, and are the same as the equivalent ones in Table 4 (the Bij).

2. Column 21 gives the sum of the estimated values of the table.

3. Column 22 gives the line constraints.

4. Column 23 gives the difference between the values of 22 and 21.

In the same way, the differences between column constraints and the sum of the estimated values for each column are given at the foot of the table.

Finally, the values calculated by means of a macro-instruction that associates the values (Cij) resulting from the calculation with the values indicated on the numbered lines (the Bij), appear on all the grey-shaded lines located above the values of the numbered lines.

For example:

If one estimates the coefficients given in line 3, taken from the original matrix, and those appearing in the line above, it can be checked in column 21 that the sum is indeed equal to 13.987, i.e. a value very close to that of the constraint, which is equal to 14 and appears in column 22. This calculation carried out for the set of the coefficients of the table shows that the method that has thus been discovered enables the calculation to be performed extremely quickly, since a simple algebraic formula now replaces the matrix formulae normally resulting from this calculation process.

Present-day calculators can deal with the corresponding problem and can even do better than this by employing calculation procedures similar to those discussed hereinbefore.

1. If the balancing calculation is performed with a table obtained by distributing the values of each zone into for example 25 micro-zones, we may find ourselves far from the line or column constraint values in two ways:

2. If boundary values are not available, then these may be evaluated by distributing the known values on the line or column, thanks to the standard definition stage (1 mm).

3. One may then proceed to a step by step calculation with steps reduced to 20 microns and operating times of the order of 1 millisecond. This method will reveal the deviations between the estimate and observation. If necessary, several fine scannings at different angles will be caried out, thereby providing several evaluations of the Cij and leading to an improvement of the desired value.

4. If the deviations between the estimate and observation are less than a threshold value fixed beforehand, a relative deviation of for example 20% will be allowed, and one can proceed without any risk to the calculation using the methods discussed above.

5. If however the deviations are higher and remain below a second threshold value, for example ±40% relative deviation, the level of expansion will be reduced by changing for example from a division of each zone into 25 micro-zones to a division of each zone into 9 micro-zones. If despite this new distribution deviations still remain within the area in question, then one will adopt a treatment according to conventional methods in order to calculate the coefficients of attenuation with certainty or, which is more economical, will adopt the method using a sequence of scannings.

6. It is thus nowadays possible to imagine using powerful but available calculators to handle mini-zones of size 1 cm×1 cm, i.e. 250 000 micro-zones of 20 microns side length, instead of 1 mm (the current resolution).

7. This resolution technique leads to an improvement of the definition by a factor of 50, and this taking into account the physical limits of the size of the blocking device and time constraints on the operation of the beam or interruption of the blocking device.

8. The example of tables 3, 4 and 5, which are similar to what might be envisaged, would involve the measurement of 35 boundary values of the beam for 300 estimated values of the coefficients of attenuation.

9. The economic and health gains are even more spectacular with larger tables.

We are however still far from the ideal situation enabling us to reach the level of a micro-zone 1 micron in size, that is to say the size of a cell.

Each of the 20-micron-size micro-zones contains in fact 8000 cells.

For the time being, these calculations would be able to reach the limit of the calculators associated with the scanner, for investigations of large zones, for example of size 20×20 cm.

It will be recalled once more that it is possible to carry out a plurality of scannings, for example a dozen scannings, which will provide for each zone a dozen close values that can then be used to calculate the mean value and the standard deviation, which in the majority of cases provides an estimate that is perfectly acceptable and avoids having to use matrix calculation, which involves prohibitive calculation times.

In order that the information can be used, it has to be edited in a suitable manner. One can proceed in a conventional way by editing maps showing for each section zones that are more or less grey depending on the coefficient of attenuation, which can be performed in two ways:

by a standard method (or by the method of multiple scannings) for the whole of the section, with a resolution of 1 mm in a complementary manner for each mini-zone treated in more detail with different shades of grey or different colours.

If necessary the mini-zones can be enlarged in order to facilitate the reading.

Advantageously it will be possible to plot lines of iso-attenuation (curves joining micro-zones having the same level of attenuation) in order to show up any particular anomalies.

By using different colours one can imagine superimposing the iso-attenuation lines on backgrounds of varying degrees of greyness.

Diagram 6-1 in the Annex shows a striking example, since apart from the use of colours, lines of levels of attenuation are plotted, which further improves the results of the investigation.

The axial scanning, that is to say the displacement of the sectional (slicing) plane, must also be taken into account, which nowadays no longer requires a real physical displacement since bars may be provided comprising a sufficient number of detectors over a length of several centimeters.

The problem is also one of processing the information since the axial displacement should be of the same order of magnitude as the scanning in a sectional plane, which involves calculations that, although largely simplified by the aforedescribed methods, must not become prohibitive.

If for reasons of detailed investigation one is led to comparing the sections, a three-dimensional projection of the information can be obtained, particularly for the micro-zones, but also for zones corresponding to the current definition.

The inventor has therefore developed a system that operates as follows:

Employ a scanner with a resolution of 1 mm in order to obtain measurements relating to zones of the same size as presently; the calculation may be carried out in two ways, either by using linear algebra, which will provide a precise value of the coefficient of attenuation of each zone, or by using the method described at the beginning, which involves ten (or multiples of ten) scannings in order to obtain a mean value and a standard deviation for each point. It is furthermore possible to carry out a larger number of scannings so as to achieve a precision that is sufficient for any point.

Define zones of more limited size for a more detailed examination (for example zones of side 1 cm, comprising 100 mini-zones per zone, i.e. a coefficient amplification of 10, or to make do with only 25 mini-zones per zone.

Distribute in each mini zone the value obtained for each zone, for example in 25 micro-zones (see Tables 3, 4 and 5). Thereby estimate the values of the coefficients of attenuation of each micro-zone and the boundary values.

Measure step by step the boundary values.

Carry out a mathematical and numerical treatment based on the use of the method described at the start of this text and shown in Table 5.

If necessary carry out the preceding operations in two or more stages so as to progressively refine the definition.

Carry out a comparitive examination of the values of the coefficients of attenuation estimated by the proportional distribution method and those calculated by the aforedescribed method. If there is a large difference in a specific micro-zone or for a set of contiguous micro-zones, the number of micro-zones per zone will be reduced and a new distribution and estimation calculation will be carried out. If the difference remains, the coefficients of attenuation for the area in question will be calculated by the conventional methods.

Edit the reference document (definition 1 mm) and the documents obtained by high definition (definition 20 to 100 microns) using new presentations such as described or envisaged above.

The process whose operation has thus been described enables a definition to be obtained that may be 100 times better than the current resolution, by using calculation techniques and tools within our reach.

Figure 22:
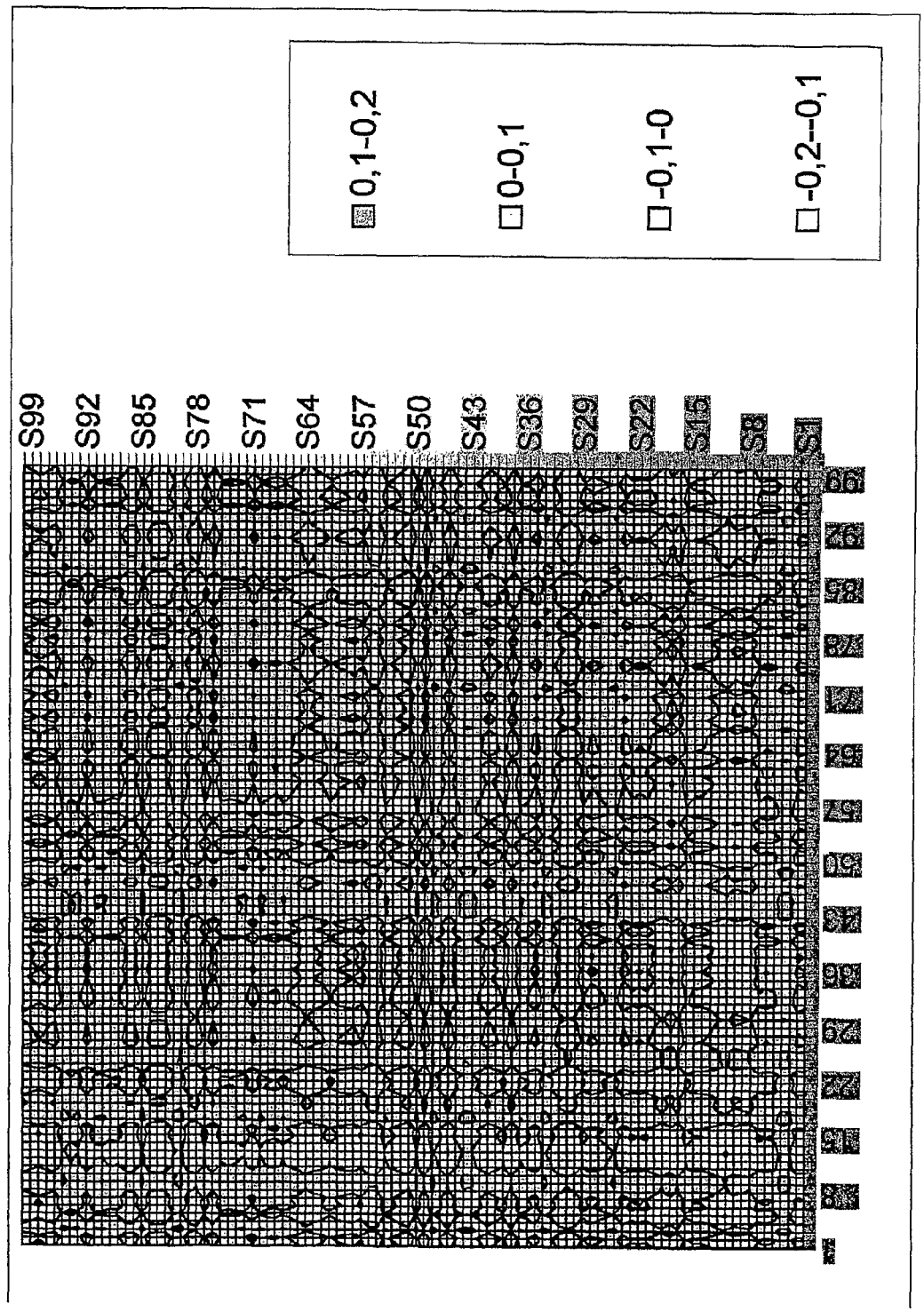
FIG. 22 is a representation of values of coefficients of attenuation obtained according to the method of the present invention at a definition of 20 microns.
Figure 23:
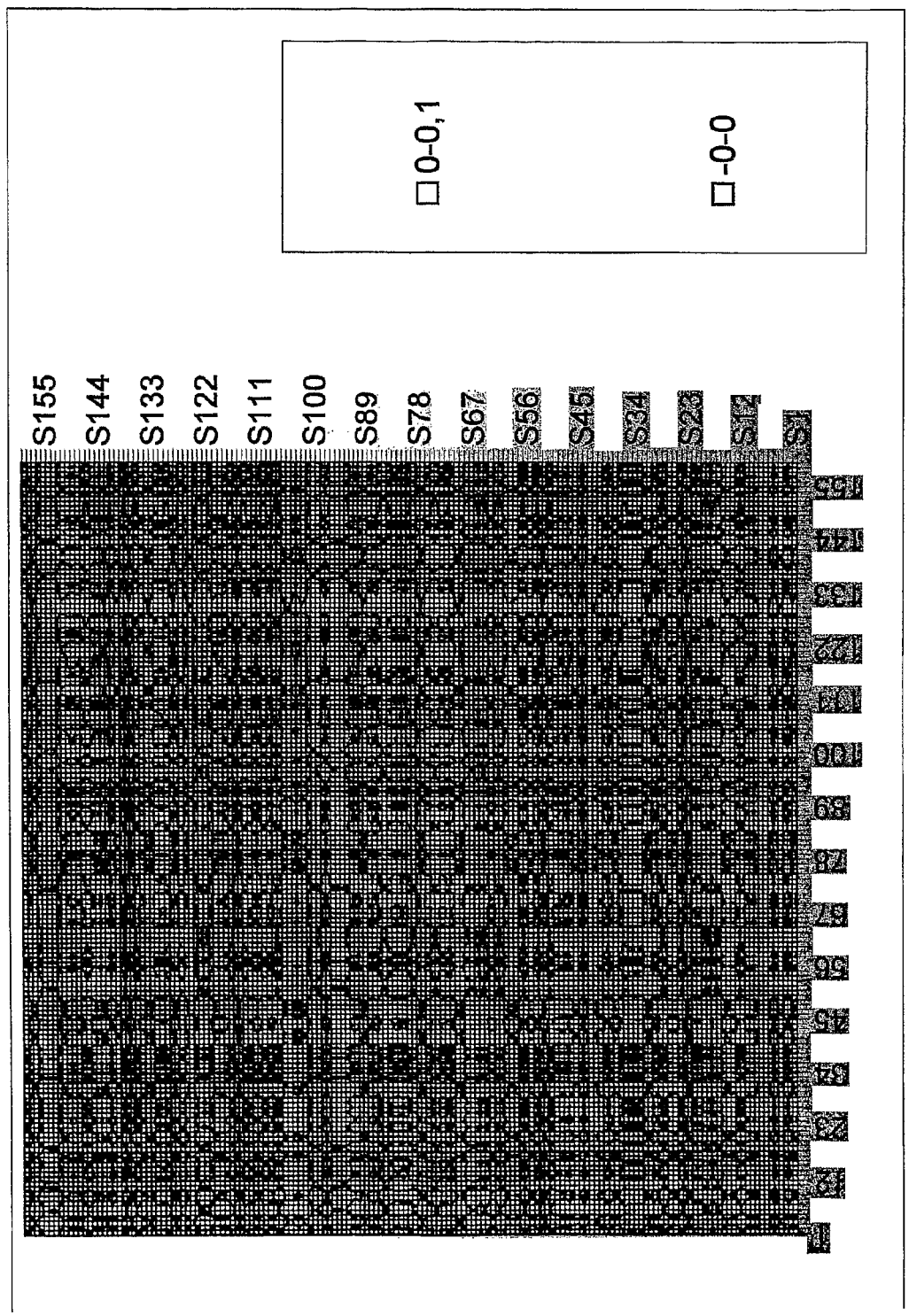
FIG. 23 is a representation of values of coefficients of attenuation obtained according to the method of the present invention at a definition of 12.5 microns.
Figure 24:
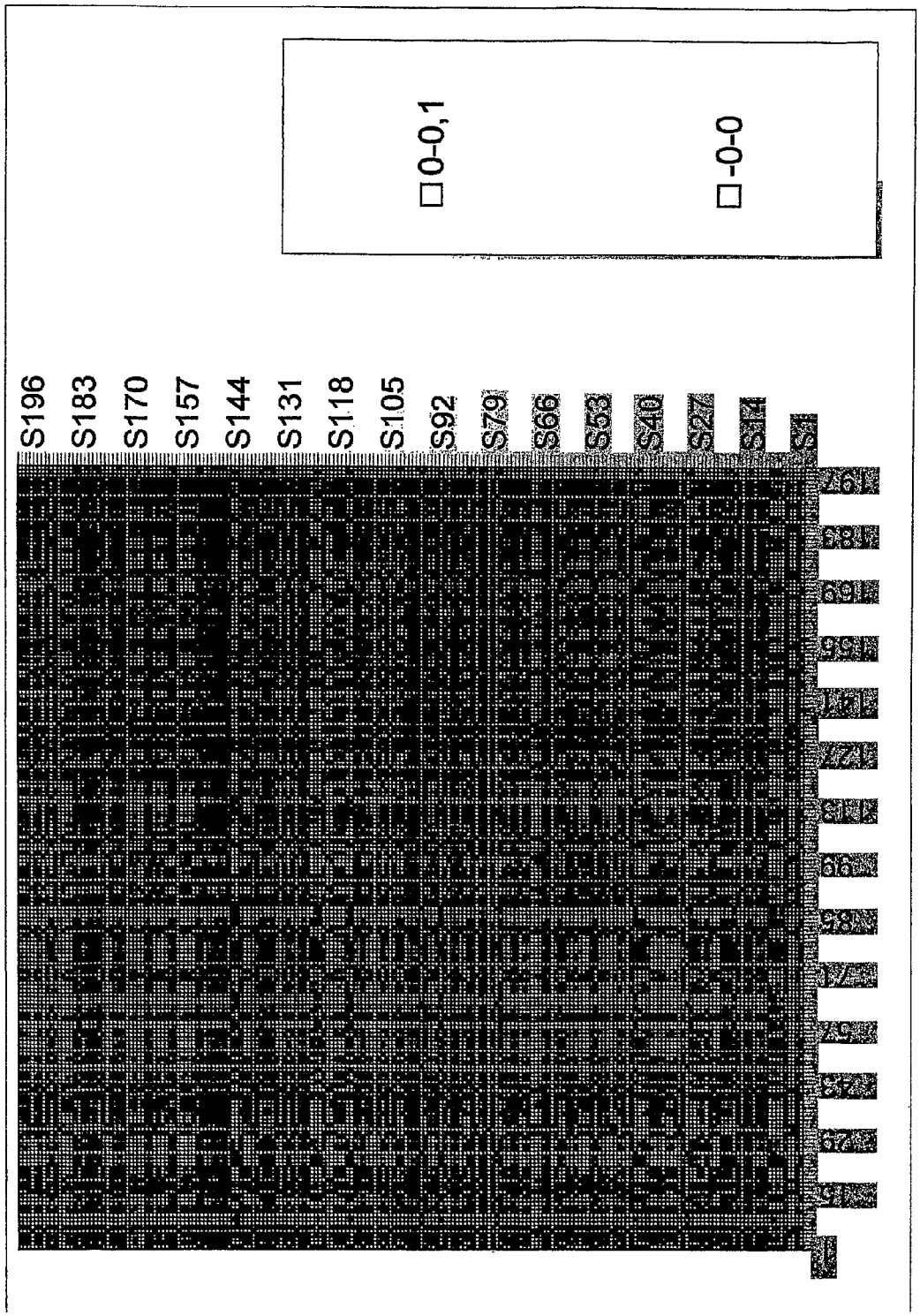
FIG. 24 is a representation of values of coefficients of attenuation obtained according to the method of the present invention at a definition of 10 microns.

Three FIGS. 22, 23 and 24 have been edited respectively for the tables 6-2, 6-3 and 6-4, showing for a reduced area images corresponding to definitions of 20, 12.5 and 10 microns. In the last case the image represents a calculation process relating to the solution of a linear algebra problem involving 40 400 equations and variables, but requiring only 400 secondary scannings, plus four primary scannings, i.e. a reduction of 99% of the irradiation level, which decreases relatively when the size of the primary area increases.

As has already been explained, an examination of a section of size 20×20 cm with a definition of 10 microns involves 400 million points and as many profiles, and requires the inversion of a 20 000×20 000 matrix by the conventional method; on the other hand our method involves only 80 000 profiles, i.e. five times fewer profiles, in two stages and using an algebraic calculation within our reach, in particular for reduced zones chosen in an appropriate manner, and this without any complication.

The technical progress in the fields of the mechanics of displacement, positioning, electrical switching and, finally, computing techniques will allow a resolution of one micron or less to be achieved, i.e. the detection of abnormal cells in an individual manner, without altering the basic principles of the described system.

Right now the techniques disclosed by the inventor in French Patent No. 00401532 relating to a microstepping (micro-toothed rack type) piezoelectric motor may be used. This process consists in causing piezoelectric bars to act via a very fine point on a mobile element, the surface of which is very finely striated so as to form a micro-toothed rack. Displacements are thus obtained with for example steps of 100 microns. However, it is also possible to use piezoelectric actuators from the CEDRAT TECHNOLOGIES company in France or from NANOMOTION in Israel so as to obtain a series of displacements involving very small steps, while benefitting from the possibility of a high output.

By way of example it is possible to use piezoelectric actuators from CEDRAT TECHNOLOGIES, known by the name APAs.

In the present case it is also possible to transmit a rotary movement by means of devices such as described by CEDRAT TECHNOLOGIES, under the name RPMs.

The methods for processing signals in order to obtain digitised images capable of benefiting from the processing methods disclosed above may obviously be used in fields other than medical imaging, in particular in the following areas:
   cartography of soils, subsoils, and atmospheric pressures,
   digital photography and cinematography and photocopying,
   the processing and transmission of images, especially in the field of television.

As regards medical imaging obtained by ultrasound echography or nuclear magnetic resonance, the process of improving the image is of the same type since, as has been explained above, the representative matrix of an image or of a specific area may consist of data associated with series of profiles focussed on one or two poles, or expressed in orthogonal or oblique co-ordinates. The expansion and/or matrix adjustment process leads in the same way to a noticeable improvement in the definition.

Figure 25:
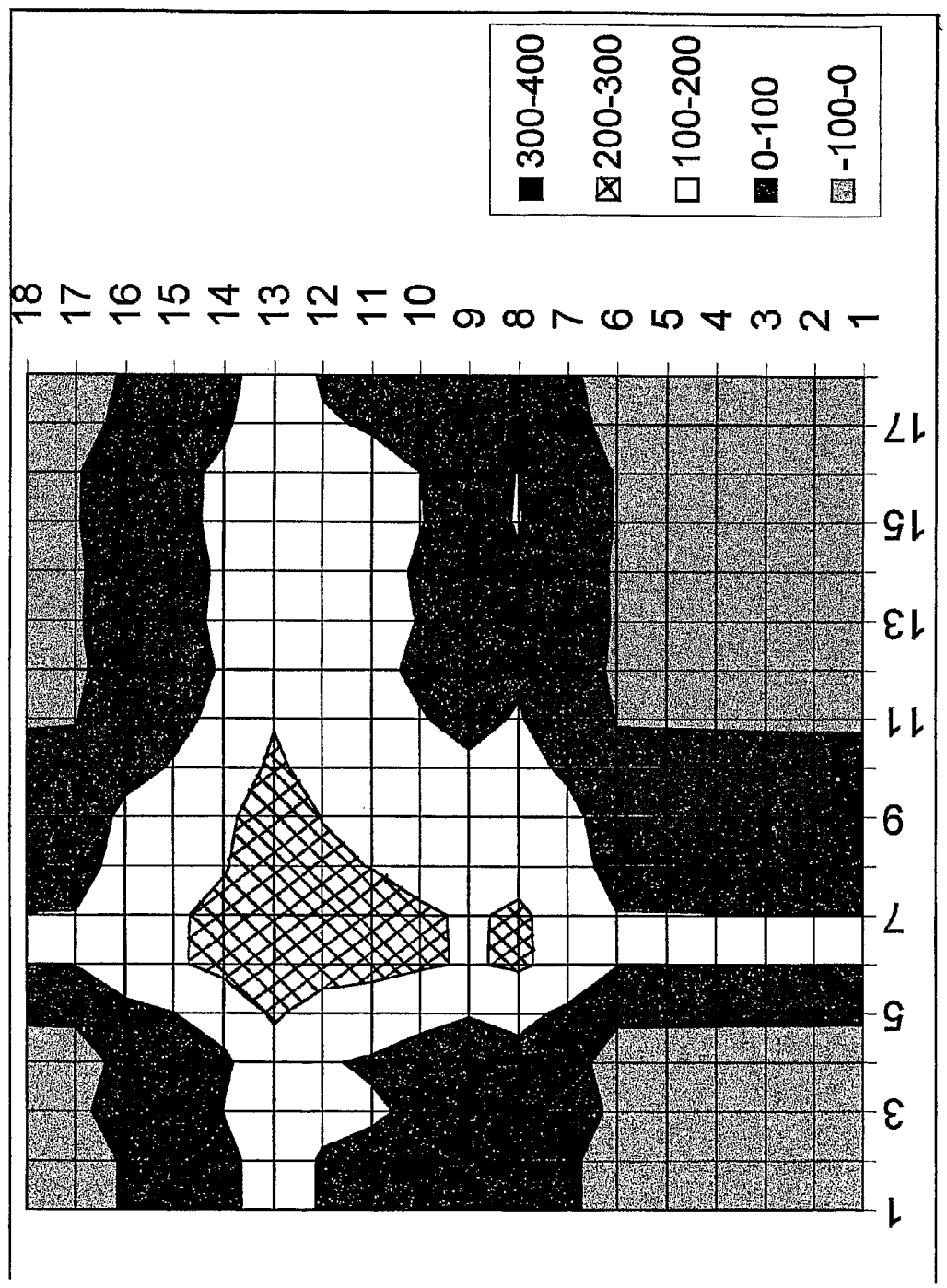
FIG. 25 is an image of a chicken bone in a sectional plan perpendicular to the longitudinal direction of the bone.

By way of experimental example, FIG. 25 shows an image of a chicken bone. The image corresponds to a sectional plane perpendicular to the longitudinal direction of the bone. The grid is graduated in millimeters and the different levels of greyness correspond to different values of the coefficient of attenuation of the bone to X-rays.

The treatment by infra-red laser or by ultrasound may also be associated with exploratory investigations.

Two systems are envisaged, differing basically in the type of displacement of the laser beam in a tomographic plane. In both cases a YAG NEODYNE laser with a wavelength of 1064 nanometers will preferably be used. The energy per pulse is between 5 and 10 millijoules. The size of the beam can be altered by the optical system, and can vary between 1 and 5 microns. The pulse duration is between 1 and 5 nanoseconds. The duration will depend in particular on the reaction time of the reading photoelectric cells. If the reaction time of the photoelectric cells is of the order of 1 microsecond, pulse times of the same order of magnitude must be provided and the energy of the beam must be appropriately adjusted. The laser device may weigh several kilograms.

It is also possible to use a fibre-optics system displaceable in the vicinity of the object to be examined and carried by an orientatable spindle that is itself displaceable on a ramp. For fine detail investigations it is possible to use a flat bundle of optic fibres, the bundle itself being displaceable and orientatable.

A first system envisages that for each plane, the laser has a fixed position and the displacement of the beam is effected by means of a mirror that is displaceable on a ramp and is orientatable by rotation at each point of its position on the ramp. A second system envisages that the laser moves on the ramp and can be oriented by rotation at each point of the ramp.

Figure 26:
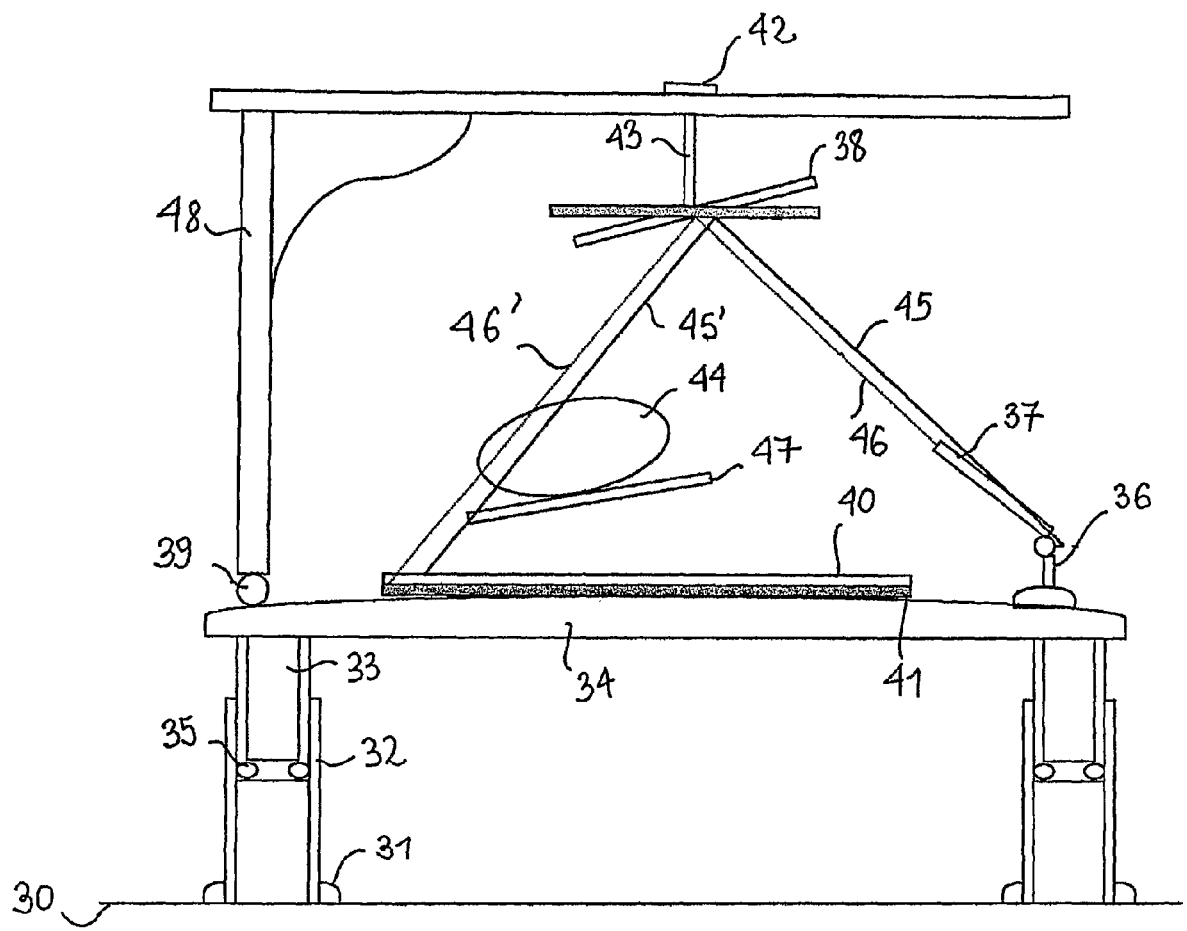
FIG. 26 is a schematic view of an apparatus according to a third embodiment of the present invention.

A view of the first system is shown in FIG. 26. In this FIG. 30 denotes a floor, 31 an adjustment means for the supporting feet of the table, 32 supporting cylinders, 33 sliding tubes, 35 Teflon toruses that enable the vibrations to be filtered out, 34 a supporting plate made of non-deformable material of rigid metal, granite or marble, so as to filter out or damp any residual vibration, 36 a means for fixing the laser on the plate, 37 a laser tube, 38 an orientatable mirror, 39 a means for fixing the bracket to the support, 41 a detection plate consisting of photoelectric cells, 42 a horizontal rail of the bracket, 40 a plate to protect the cells against over-exposure, 43 a supporting rod for the mirror, 44 an object to be examined, 45 or 46 an incident laser ray, 45' or 46' a parallel laser ray, 47 a rotatable, displaceable supporting plate for the object to be examined, and also transparent to infra-red radiation, and 48 denotes a bracket.

The operation is as follows. The supporting plate 47 is placed at the desired height by moving, within the supporting cylinder 32, the sliding tube 33 and a small plate for supporting torus-shaped joints 35. The sliding tube 33 has no contact with the supporting cylinder 32 other than through the Teflon torus-shaped joint 35, which filters practically all vibrations. The supporting rod 43 for the mirror 38 is displaced to the required position, and the mirror 38 and the laser 37 are oriented so that the incident laser ray 45 is oriented as desired.

Various scanning programs enable low definition or high definition profiles to be obtained. In the first case, the elementary surface of each cell is of the order of 1 mm$^2$. In the second case the size of the elementary cell may be of the order of 100 microns and may be as little as 1 micron (practical limit taking into account the wavelength).

In order to obtain the desired definition, the beam is passed through an optics system integrated in the laser tube, enabling its diameter at the level of the object to be examined to be increased up to 1 mm or to be reduced to 1 micron.

In the case of small diameters two procedures may be adopted, jointly or otherwise, by performing the operation so that the duration of a pulse is reduced in order to decrease the thermal effects on the objects to be traversed or on the photoelectric cells, or by inserting a device 40 for absorbing the infra-red energy. The formation of a tomographic plane will thus be effected as follows:

In the first stage the beam will be regulated and the detection plate will be adjusted so as to operate for example at a definition of 1 mm, and a scanning program will be defined so as to obtain a number of profiles equal to the surface in mm$^2$ of the section of the object, and the scanning program will be executed by transferring the results obtained from the cells to the computer.

In the second stage, the beam and the detection plate will be regulated so as to obtain the desired high definition, and a crossed scanning program will be established depending on the zone to be explored in the cross-section of the object, on the angle (generally a right-angle) between two parallel high definition or non-high definition scannings, and on the opacity of the object, so as to regulate the duration of the pulses and the possible absorption.

The data obtained at the cellular level will be transferred to the computer, which will carry out the data processing and store the results.

In the third stage, the results of the calculation will be used to produce an image of each tomographic plane by means of a printer using (or not) scales of greyness or colours.

The use of the previously described algorithm will take place under identical conditions. The process thus used permits a very considerable saving in calculation time in proportions identical to those obtained for the X-ray scanner.

In the chosen mode of operation the mirror 38 pivots about an axis of rotation, in the same way as the laser beam, so as to obtain parallel traversing rays 46 and 46'. The mirror will be able to be moved a sufficient distance so as to obtain two series of profiles such that in each series the traversing rays are parallel to one another and the two series intersect, and in a new scanning at a different angle the two parallel scannings intersect.

The volume of a singularity will be able to be obtained by simply counting in a given plane the small squares having a certain level of colouration, and then adding the numbers obtained in the adjacent planes and for adjacent zones, between two limiting planes defined by observation.

The database consisting of the set of results relating to the different planes will be able to reveal the black zones resulting from the absolute opacity of certain inclusions, which would prevent certain zones thus hidden from being seen.

In order to illuminate this zone two ways at least can be adopted, namely either to turn the object to be examined so as to obtain a plurality of images at different angles after having placed in position microscopic reference elements so as to reconstitute a complete image, or to turn the bracket 48 so as to obtain images of hidden zones.

In both cases the object to be examined should be placed on and if necessary fixed to the transparent plate 47, which is capable of turning about an axis.

In this first system the reflection by the mirror becomes difficult for certain wavelengths, resulting in losses of light energy that may vary with the angle of reflection, which can complicate the calculation by requiring that more complex reference measurements be made in the absence of the object.

On the other hand, the rotation and the translation of the mirror 38 is greatly facilitated by its low weight, and only requires low power piezoelectric actuators.

Figure 27:
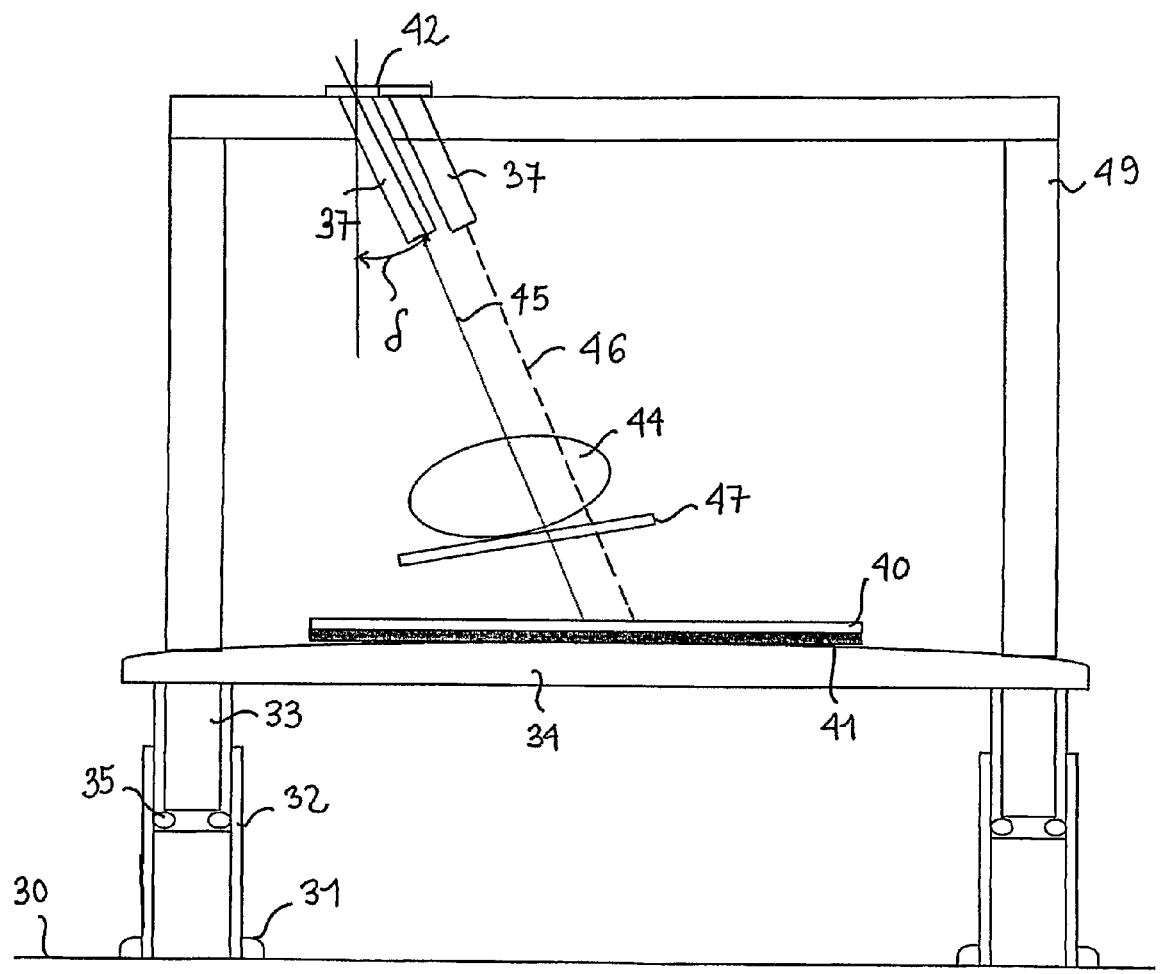
FIG. 27 is a schematic view of an apparatus according to a fourth embodiment of the present invention.

A view of the second system is shown in FIG. 27, in which identical reference numerals denote identical elements. The reference numeral 49 denotes a frame.

The functioning of the system is as follows.

The supporting plate 34 is placed at the desired height by moving within the interior of the supporting cylinder 32 the sliding tube 33 and a small supporting plate for torus-shaped joints 35. The plate 47 for supporting the object to be examined is positioned at the chosen angle. The same procedure as for the first system is then followed. In order to illustrate the scannings reference will be made to FIG. 18, which shows the displacement of the beam 37 at a distance from a first position and the choice of a new inclination of the beam 37 so as to obtain two intersecting scannings. The beams 45 and 45' are parallel to one another in each of the scannings.

In this second system the translation and the rotation of the laser beam 37 require more powerful actuators. In this case too the use of the previously described algorithm will provide the same advantage. The process that is thus used will permit a very considerable saving in calculation time of the same order as that obtained for an X-ray scanner.

It may be noted that the attenuation may, in the case of infra-red radiation, be the result of several phenomena, such as reflection inside the object, a refraction in specific zones, and absorption of the infra-red energy converted into heat.

It will therefore be important to measure also the rise in temperature, where this is possible, in different zones, so as to distinguish the various sources of attenuation.

The nature of the object is then important, and the possibility of being able to turn the object for different measurements enables useful information to be obtained in evaluating errors resulting from reflection or refraction, which depend on the wavelength and the corresponding refractive index for the different materials.

In order to avoid reflection phenomena it is possible to produce a thin layer of material of low refractive index by vapour phase deposition on a very thin film of plastics material and to cover the organism with this film 50.

Figure 28:
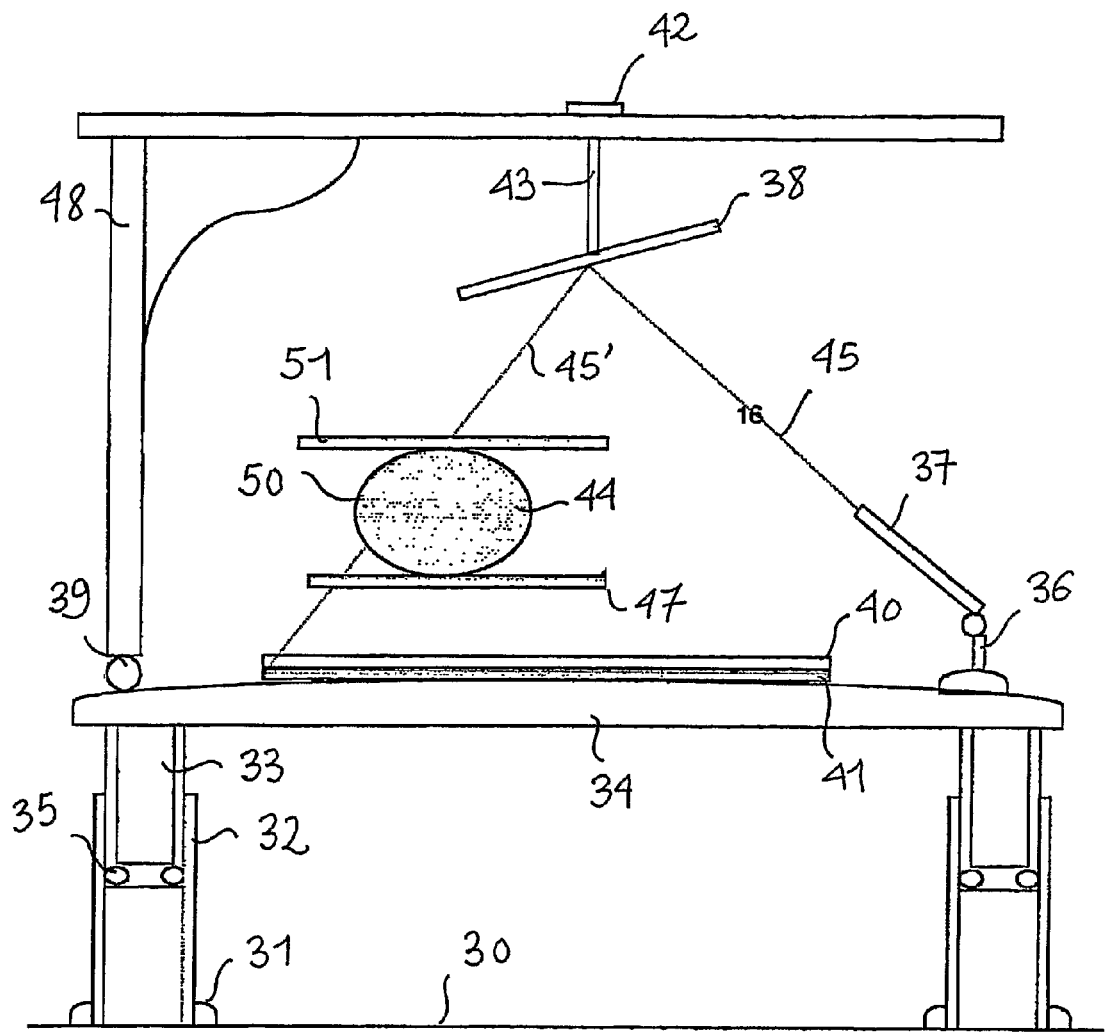
FIG. 28 is a schematic view of a variant of the apparatus shown by FIG. 26.

As regards refraction, in the case where a laser is used, that is to say coherent light is produced, the phenomenon may be different to when a non-coherent light is used, though there still exists a certain degree of refraction that can be reduced, FIG. 28, by arranging the organism or object 44 between two transparent plates 47 and 51, one of the plates forming the support plate described in the examples illustrated in FIGS. 26 and 27, coated with anti-reflecting layers so as to avoid reflection, and which are also strictly parallel so as to limit the refraction that they may cause.

Nevertheless a certain refraction is possible within the body 44, which may lead to a deviation of the beam. In this case the organism is enveloped by the ultra-thin plastics film 50 coated with an anti-reflecting layer, the two transparent plates 47 and 51 are arranged at the necessary distance above one another, a calibration test is carried out which enables the beam to be localised without the organism 44 for different scanning angles, and a regular scanning of the organism is performed to measure the deviation of each beam that the organism produces.

If there is no deviation or if the deviation is regular, the image obtained will be of an acceptable quality. If there is an irregular deviation, a correction will be necessary in order to re-adjust the image, taking into account the initial angle of incidence, and after a normal rectification a matrix will thus be processed in this way, each line of which will be replaced in order to correct the deviation.

This problem disappears for X-rays, for certain angles of incidence, for infra-red radiation, or if the traversed body includes zones with similar refractive indices. In the case where differences are found, resulting from large variations of refractive indices, the following procedure will be adopted:

a) an analysis of a specific zone is carried out using an X-ray scanner. This analysis enables differences in the type of tissue or singularities in the analysed zone to be detected.

b) In this small, perfectly identified zone a scanning is carried out using a very high definition infra-red laser, and the corresponding information is collected in order to prepare a map of the analysed zone, obtained by the infra-red scanning using a heuristic treatment of the path of each ray taking account of an evaluation of the refractive index of each of the traversed micro-zones, resulting both from data obtained by the X-ray scanner as well as from a knowledge of the co-ordinates of the initial point and of the final point of the path through the zone.

Thus, the combination of the two systems, namely X-ray scanner or infra-red laser scanner, leads to an improvement of the image quality and of its definitions.

However, in the two infra-red scanner systems described here, the method according to the invention allows the number of profiles to be obtained by infra-red laser to be reduced to such an extent for high definitions that the rise in temperature will still be controllable, thereby avoiding an excessive heating of the investigated object or organism, or if the traversed body comprises zones whose refractive indices are similar.

As has already been explained, the calculation times will remain within the limits of the normal methods for processing the information.

The invention claimed is:

1. An imaging method involving a X-rays or infrared light beams to irradiate a body and signal processing to obtain representative images of values associated with each zone of a sectional plane of the body, with the aid of an imaging device comprising a source and a detector, in which, crosswise scannings in the sectional plane of the body are carried out a variation of intensity of the X-ray or infra-red light beams between the source and the detector is measured along scanning profiles, and by means of a programmed computer, i) initial values coefficients of attenuation are calculated for a number of zones of the sectional plane of the body equal to the crosswise scannings, and a low definition initial image of said sectional plane is constructed from an initial matrix of initial values, in order to obtain a high definition image, wherein, a first and a second series of supplementary scannings of the sectional plane of the body are carried out, the scannings of the first series being crossed with respect to the scannings of the second series, a variation of intensity of the X-ray or infrared light beam between the source and the detector is measured along respectively n and m scanning profiles of the first and the second series, and by means of the suitably programmed computer, ii) an expanded rectangular matrix is constructed from the initial matrix, comprising n lines and m columns of values estimated by making an interpolation between the values associated with two zones, or by dividing a zone up into micro-zones and distributing in the micro-zones the value associated with this zone, in which the m values of the n lines correspond to the m interpolated values or to the m micro-zones along n scanning profiles derived from the first scanning series, and in which the n values of the m columns correspond to the n interpolated values or to the n micro-zones along the m scanning profiles derived from the second scanning series, iii) n and m line and column boundary values of the expanded matrix are calculated, representative of the high definition image, in which a line boundary value is the sum of the m terms of a line and in which a column boundary value is the sum of the n terms of a column, and iv) each of the n times m terms of the expanded matrix is adjusted using a least squares method of adjustment, taking into account the line and column constraints relating to the boundaries of the expanded matrix, in which the n line constraints are determined by the variation of intensity of the X-ray or infra-red light beams along the n scanning profiles derived from the first scanning series, and in which the m column constraints are determined by the variation in intensity of the X-ray or infra-red light beams along the m scanning profiles derived from the second scanning series, and by using the following formula:

$$C_{ij} = B_{ij} + \frac{1}{n}\left(\rho_j - \sum_{i=1}^{n} B_{ij}\right) + \frac{1}{m}\left(c_i - \sum_{j=1}^{m} B_{ij}\right) - \frac{1}{nm}\left(\sum_{j=1}^{m}\rho_j - \sum_{i=1}^{n}\sum_{j=1}^{m} B_{ij}\right)$$

where, in this formula,
Cij is the sought value,
Bij is the initially estimated value
(n) is the number of lines of the rectangle matrix
(m) is the number of columns of the rectangle matrix $$\sum_{i=1}^{n} C_{ij} = \rho_j$$

for all the values of i, the constraint of the column j $$\sum_{j=1}^{m} C_{ij} = c_i$$

for all the values of j, the constraint of the line i, so as to obtain the n times m values representative of the high definition image by a number of supplementary scanning profiles limited to n plus m and thereby reduce the exposure of the body to X-rays or infra-red light beams while increasing the definition of the image.

2. The method according to claim 1, in which the crossed first and second series of supplementary scannings are carried out several times at different angles of the sectional plane of the body, and in which steps ii), iii) and iv) are carried out each time so as to obtain a series of evaluations of the value representative of the high definition image, and to calculate a mean value of the measurements and estimate a standard deviation.

3. An Apparatus for implementing a method according to claim 1 comprising:

a support for receiving a body to be examined,
a source emitting a X-ray or infrared light beams onto the body to be examined
a detector for detecting intensity attenuated according to thee passage of the X-ray or infra-red light beams by the source through the body to be examined,
the beams being emitted along different direction so as to carry out crosswise scannings of a sectional plane of the body and to measure a variation in intensity of the X-ray or infrared light beams between the source and the detector long scanning profiles and comprising, a computer programmed to:

i) calculate initial values coefficients of attenuation for a number of zones of the sectional plane of the body equal to the crosswise scannings, and construct a low definition image of said sectional plane from an initial matrix of initial values, in order to obtain a high definition image, wherein, the computer is programmed to:

ii) construct an expanded rectangular matrix is constructed from the initial matrix, comprising n lines and m columns of values estimated by making an interpolation between the values associated with two zones, or by dividing a zone up into micro-zones and distributing in the micro-zones the value associated with this zone, in which the m values of the n lines correspond to the m interpolated values or to the m micro-zones along n scanning profiles derived from the first scanning series, and in which the n values of the m columns correspond to the n interpolated values or to the n micro-zones along the m scanning profiles derived from the second scanning series, iii) calculate n and m line and column boundary values of the expanded matrix, representative of the high definition image, in which a line boundary value is the sum of the m terms of a line and in which a column boundary value is the sum of the n terms of a column, and iv) adjust each of the n times m terms of the expanded matrix using a least squares method of adjustment, taking into account the line and column constraints relating to the boundaries of the expanded matrix, in which the n line constraints are determined by the variation of intensity of the X-ray or infra-red light beams along the n scanning profiles derived from the first supplementary scanning series, and in which the m column constraints are determined by the variation in intensity of the X-ray or infra-red light beams along the m scanning profiles derived from the second supplementary scanning series, and by using the following formula:

$$C_{ij} = B_{ij} + \frac{1}{n}\left(\rho_j - \sum_{i=1}^{n} B_{ij}\right) + \frac{1}{m}\left(c_i - \sum_{j=1}^{m} B_{ij}\right) - \frac{1}{nm}\left(\sum_{j=1}^{m} \rho_j - \sum_{i=1}^{n} \sum_{j=1}^{m} B_{ij}\right)$$

where, in this formula,
$C_{ij}$ is the sought value,
$B_{ij}$ is the initially estimated value
(n) is the number of lines of the rectangle matrix
(m) is the number of columns of the rectangle matrix $$\sum_{j=1}^{n} C_{ij} = \rho_j$$

for all the values of i, the constraint of the column j $$\sum_{j=1}^{m} C_{ij} = c_i$$

for all the values of j, the constraint of the line i, so as to obtain the n times m values representative of the high definition image by a number of supplementary scanning profiles limited to n plus m and thereby reduce the exposure of the body to X-rays or infra-red light beams while increasing the definition of the image.

4. The apparatus according to claim 3, wherein it comprises a guidance by means of piezoelectric actuators displacing the source or a mirror reflecting an infra-red beam emitted by the source, step by step in a linear manner so as to carry out the first and the second series of supplementary scannings.

5. The apparatus according to claim 4, wherein the mirror is displaced by rotation about a pivotal point, by means of piezoelectric actuators, to reflect an infra-red laser beam so as to obtain coefficients relating to each scanning profile derived from the first and the second series of supplementary scannings, corresponding to a given step of the linear displacement of the mirror.

6. The apparatus according to claim 4, wherein the source pivots about an axis that itself moves linearly by means of piezoelectric actuators.

7. The apparatus according to claim 3, wherein it comprises multiple detection bars for producing simultaneously a plurality of parallel images capable of individual processing or processing in three dimensions.

8. The apparatus according to claim 3, wherein it comprises two perpendicular sources in order to carry out the supplementary scannings of the first series perpendicular to the supplementary scannings of the second series.

9. The apparatus according to claim 4, wherein it comprises plates or other supports for X-ray or infra-red laser beam, on which the piezoelectric actuators enable the beam to be oriented or to be displaced, so as to obtain by means of the array of the detectors, information relating to the attenuation of each scanning profile of the first and second supplementary scanning series, produced by a step of the beam.

10. The apparatus according to claim 4, wherein it comprises perforated blocking plates which may be shielded by two crossed networks of displaceable wires or strips so as to effect one or more unblockings by displacement of the plates or strips.

11. The apparatus according to claim 4, wherein it comprises two transparent plates coated with anti-reflecting layers to prevent a reflection of the infra-red beam and which are parallel in order to limit a refraction of this beam, the body to be examined being arranged between the two plaques and resting against one of them serving as support plate.

12. A programmed computer for carrying out stages (i) to (iv) of a method according to claim 1.

13. A non-transitory computer readable medium encoded to carry out stages (i) to (iv) of a method according to claim 1 when it is loaded in a computer.

* * * * *